(12) United States Patent
Marshall

(10) Patent No.: US 6,250,925 B1
(45) Date of Patent: Jun. 26, 2001

(54) DENTAL PROSTHESIS WITH MULTI-SECTION INFRASTRUCTURE AND METHOD FOR REPLACEMENT OF TEETH

(75) Inventor: Howard B. Marshall, New York, NY (US)

(73) Assignee: Oro-Health International, Inc., New York, NY (US)

( * ) Notice: Subject to any disclaimer, the term of this patent is extended or adjusted under 35 U.S.C. 154(b) by 0 days.

(21) Appl. No.: 09/371,376

(22) Filed: Aug. 10, 1999

Related U.S. Application Data

(62) Division of application No. 08/881,027, filed on Jun. 23, 1997, now Pat. No. 5,934,907.

(51) Int. Cl.[7] .................................................. A61C 13/22
(52) U.S. Cl. ............................................................ 433/181
(58) Field of Search .................................. 433/180, 181, 433/182, 191–195

(56) References Cited

U.S. PATENT DOCUMENTS

| | | |
|---|---|---|
| 2,213,963 | 9/1940 | Myerson . |
| 2,491,581 | 12/1949 | Reichner . |
| 2,826,814 | 3/1958 | Sappey et al. . |
| 4,380,435 | 4/1983 | Raeder et al. . |
| 4,445,862 | 5/1984 | Chiaramonte et al. . |
| 4,457,714 | 7/1984 | Klein . |
| 4,475,891 | 10/1984 | Hader . |
| 4,583,948 | 4/1986 | Jansen . |
| 4,661,067 | 4/1987 | Harvey, Sr. et al. . |
| 4,689,013 | 8/1987 | Lustig . |
| 4,713,005 | * 12/1987 | Marshall et al. ..................... 433/180 |
| 4,764,116 | 8/1988 | Shoher et al. . |
| 4,775,320 | 10/1988 | Marshall et al. . |
| 4,781,592 | * 11/1988 | Fukutsuji ............................ 433/181 |
| 4,813,873 | 3/1989 | Seaton . |
| 4,820,157 | 4/1989 | Salvo . |
| 4,826,436 | 5/1989 | Shoher et al. . |
| 4,950,162 | 8/1990 | Korber et al. . |
| 4,957,439 | 9/1990 | Shoher et al. . |
| 5,007,836 | 4/1991 | Gayso . |
| 5,092,772 | 3/1992 | Seaton . |
| 5,934,907 | * 8/1999 | Marshall ............................ 433/181 |

* cited by examiner

*Primary Examiner*—Ralph A. Lewis
(74) *Attorney, Agent, or Firm*—Lerner, David, Littenberg, Krumholz & Mentlik, LLP

(57) ABSTRACT

An improved dental prosthesis for replacing a tooth or teeth in an edentulous space in a patient's mouth either adjacent to existing teeth or between a first tooth anterior of and a second tooth posterior of the edentulous space which tooth or teeth are prepared with occlusal mounting grooves and where indicated indentations on the respective buccal and lingual proximals of the same tooth or teeth for receiving said dental prosthesis; has multi-section infrastructure for fabricating the dental prosthesis which includes, a main support bar or beam having a sized and shaped center section and at least one connecting end for fastening the main support bar on the tooth or teeth adjacent the edentulous space, the connecting end or ends has a predetermined shape, material and is sized to permit adjustment thereof as a function of the mesial-distal length of the edentulous space and the relative position of the tooth or teeth adjacent the edentulous space, secondary support means operatively connected to the main support means includes, longitudinally extending side grooves formed on the buccal and lingual sides of the center section, and side buttresses are positioned and connected in the respective side grooves. Optionally, a generally U-shaped pontic clip is adjustably positioned in vertically disposed grooves on the center section to adjust the occlusal surface of the main support bar relative the gingiva of the edentulous space.

24 Claims, 21 Drawing Sheets

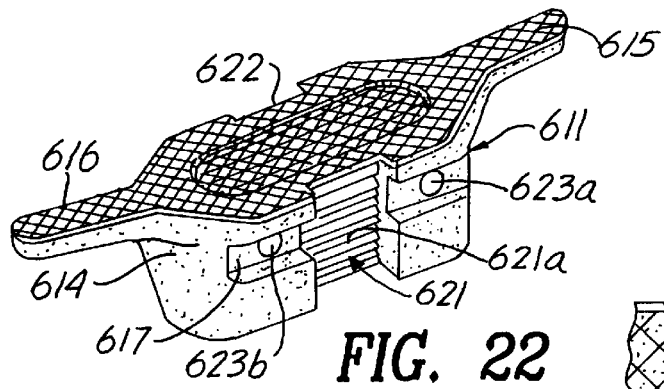
FIG. 22
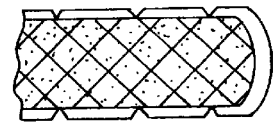
FIG. 23A
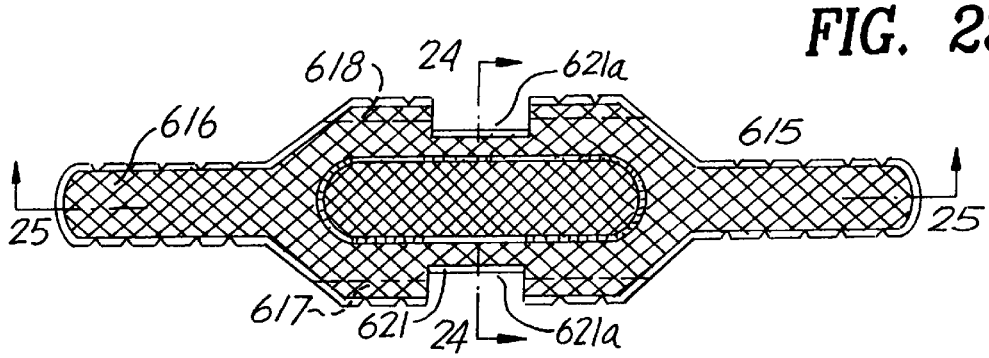
FIG. 23
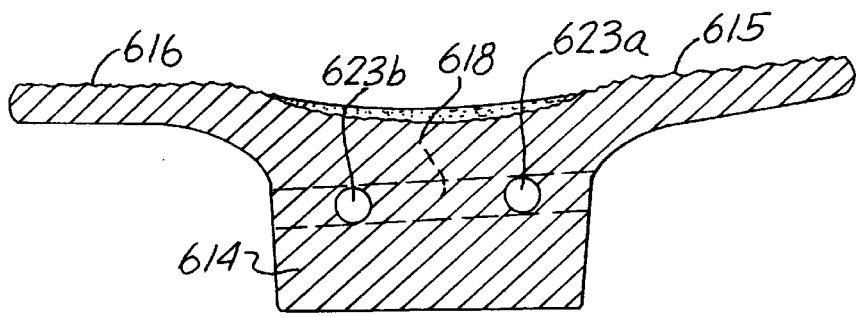
FIG. 25
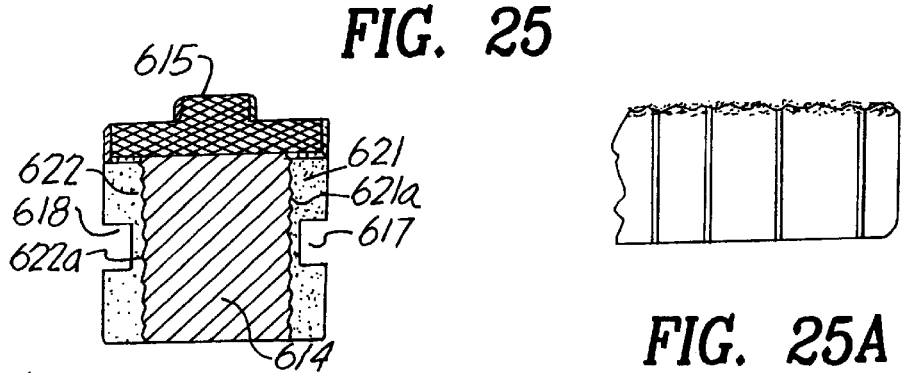
FIG. 24
FIG. 25A

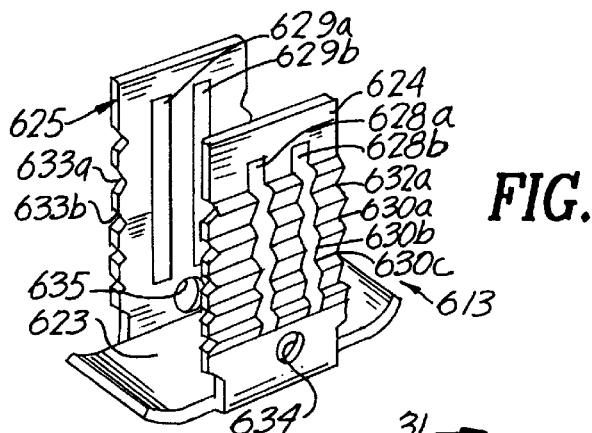
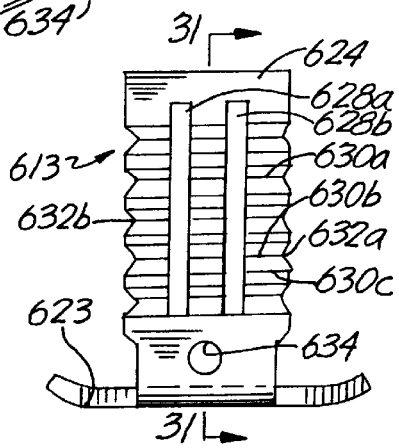
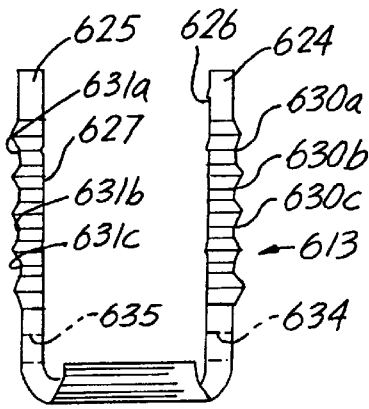
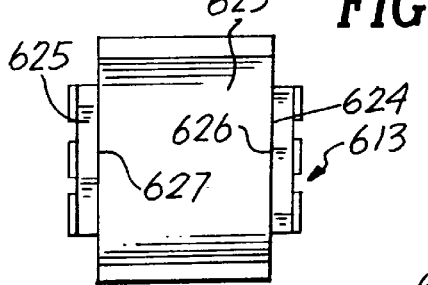
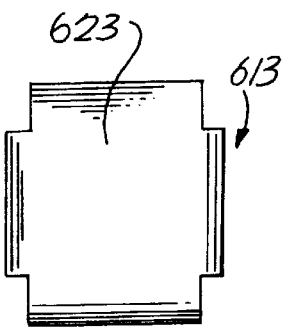
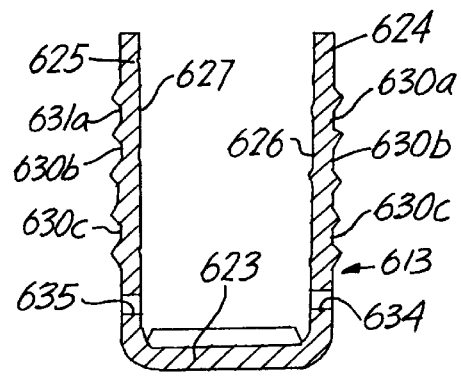
FIG. 26
FIG. 27
FIG. 28
FIG. 29
FIG. 30
FIG. 31

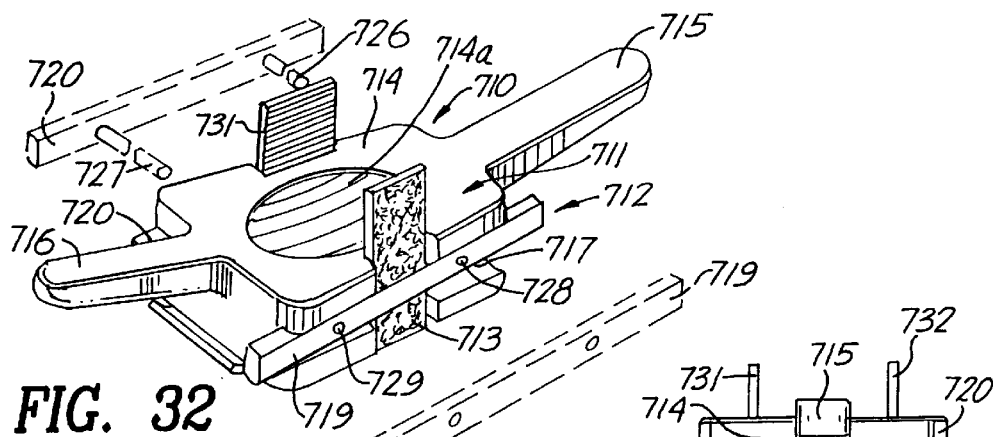
FIG. 32
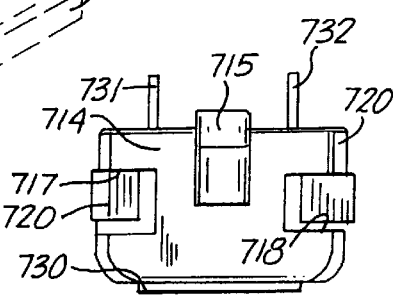
FIG. 34
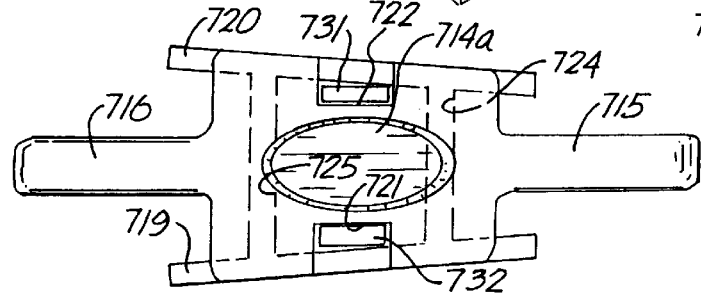
FIG. 33
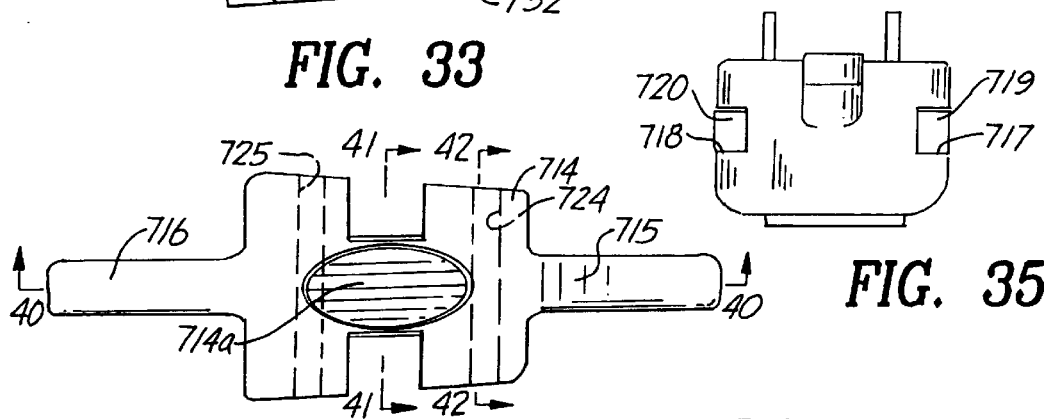
FIG. 35
FIG. 36
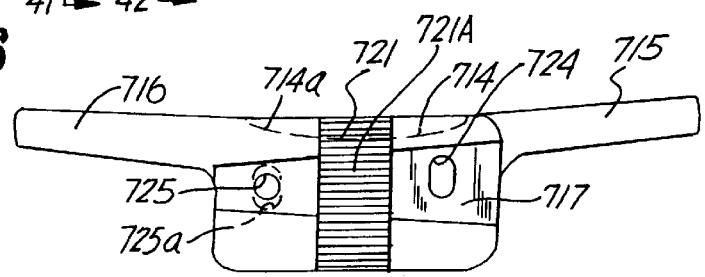
FIG. 37

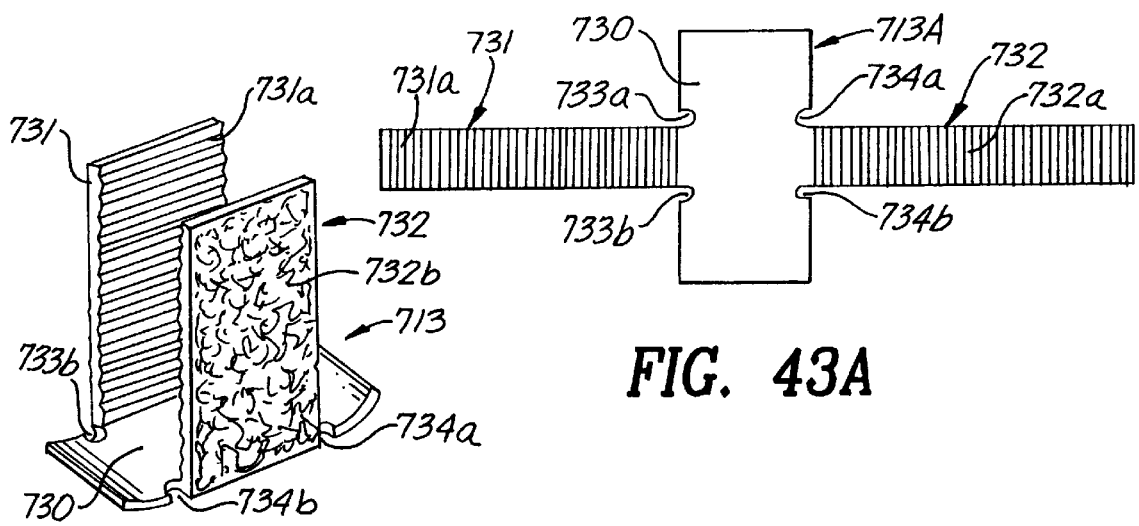
FIG. 43
FIG. 43A
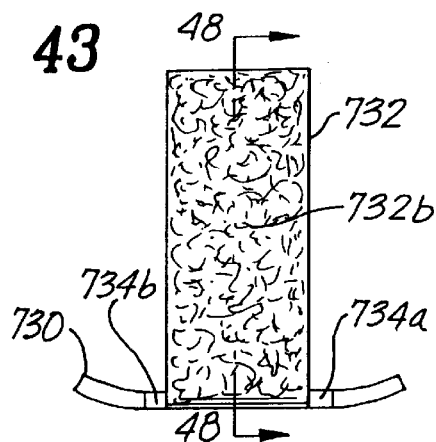
FIG. 44
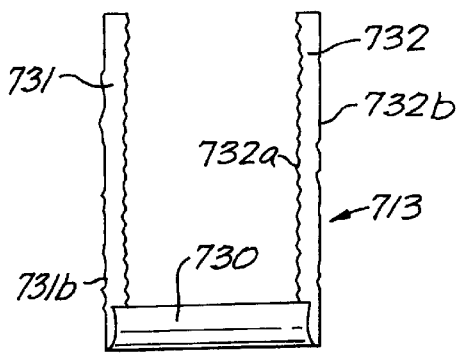
FIG. 45
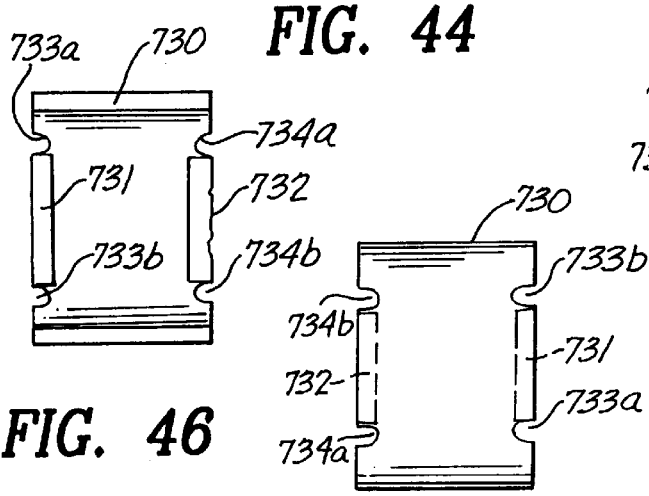
FIG. 46
FIG. 47
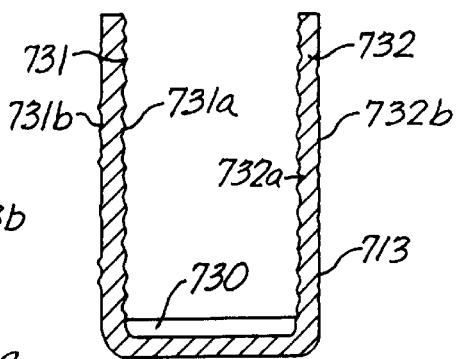
FIG. 48

DENTAL PROSTHESIS WITH MULTI-SECTION INFRASTRUCTURE AND METHOD FOR REPLACEMENT OF TEETH

This application is a divisional application of application Ser. No. 08/881,027 filed Jun. 23, 1997 now U.S. Pat. No. 5,934,907.

This invention relates generally to dental prostheses and more particularly to a dental prosthesis having multi-section infrastructure to strengthen the dental prosthesis and to provide a simple, relatively low cost, improved fixed bridge and method for the replacement of a tooth or teeth in an edentulous space adjacent to or between existing teeth in a patient's mouth.

U.S. Pat. Nos. 4,713,005 and 4,775,320 disclose a substantial portion of the existing prior art for forming a dental prosthesis and the use thereof for the replacement of a pontic or pontics in an edentulous space or spaces adjacent to or between the teeth in a patient's mouth.

These patents and other patents which they identify disclose dental prostheses using longitudinally extending bridge bars affixed generally into the occlusal surfaces in the patient's teeth adjacent to the edentulous space, as the main support for the pontic or pontics to fill the edentulous space or spaces adjacent to or between the patient's teeth.

The purpose and object of all these prior art fixed bridge pontic replacement assemblies and methods are designed to simplify the procedures for the Dentist to replace missing teeth, reduce the time required for accomplishing such replacement and the cost of such dental prosthesis to the patient.

Thus, in U.S. Pat. Nos. 4,713,005 and 4,775,320, an improved dental prosthesis and method for fabricating the pontic or pontics for replacement of a tooth or teeth in an edentulous space disposed either adjacent to an existing tooth or between existing teeth, utilizes a longitudinally extending bridge bar having at least one connecting member or end which is fixedly mounted in groves cut in the occlusal surface of the adjacent existing teeth, and a centrally located boss on which a pontic base is adjustably and operatively connected.

When this bridge bar, boss and pontic base are in position in the occlusal grooves in the adjacent existing tooth or teeth in respect of the edentulous space adjacent to or between the patient's teeth and the pontic base has been properly adjusted relative to the occlusal surface of the gum line in the edentulous space, the pontic or pontics, when formed about the bridge bar, centrally located boss and pontic base in accordance with the method as further disclosed therein, will lightly touch the occlusal surface of the gum with the polished outer surface of the pontic base.

Two methods are described in U.S. patents '005 and '320 for fabricating the dental prosthesis with the pontic or pontics to provide the replacement tooth or teeth for the edentulous space in the patient's mouth. One method establishes the dental prosthesis with the pontic replacement thereon by "in situ" procedures in the patient's mouth. The other method utilizes a suitable model of the edentulous space and the associated tooth or teeth, which model is used exteriorly of the patient's mouth to establish the dental prosthesis having a pontic or pontics. The dental prosthesis so formed on the models are then transferred into the patient's mouth, and then the dental prosthesis is finished, set and polished.

The dental prosthesis and method in accordance with the present invention for the replacement of a tooth or teeth in an edentulous space adjacent to or between the tooth or teeth in a patient's mouth has an improved multi-section infrastructure which is critical because it enables the pontic or pontics formed thereon which span the edentulous space to withstand the enormous vertical, horizontal and more particularly the rotational forces exerted on the teeth during mastication, clenching of the jaws and nocturnal grinding of the teeth without flexing or deforming.

This improved multi-section infrastructure consists generally of, a longitudinally extending main support bar having, a shaped and sized center section, at least one connecting end or oppositely projecting connecting ends for connecting the main support bar into the prepared occlusal surface or surfaces in the tooth or teeth adjacent to the edentulous space so the shaped and sized center section can be centered in the edentulous space, and secondary support means such as spaced buttresses operatively connected on opposite sides of the shaped and sized center section of the main support bar and disposed to engage indentations cut in the tooth or teeth in which the main support bar is mounted provide three points of contact to prevent torque or rotation of the dental prosthesis when it is in assembled position.

This shaped and sized center section in assembled position is in a plane slightly more gingival than the relative plane or planes of the connecting end or ends of the main support bar. Thus, if the edentulous space is in the lower jaw, the occlusal surface of the shaped and sized center section is lower than connecting ends, and in the upper jaw the occlusal mid surface of the shaped and sized center section will be superior to the connecting ends. Additionally, the actual position of the medial occlusal surface of the shaped and sized center section is also a function of how deeply the preparations are drilled in the occlusal surface or surfaces and whether such respective preparations are equal in depth from the respective occlusal surfaces of the tooth or teeth to which the shaped and sized center section is connected. The length of the connecting end or the oppositely extending connecting ends are adjustable by grinding or by cutting. The angles of the connecting and/or the oppositely extending connecting ends are adjustable with a simple pliers to accommodate for various differences and degrees of tilting of the supporting tooth or teeth and for relative curvatures at various sections of the supporting teeth in a patient's mouth.

As also will be clear to those skilled in the art from the description of the various species of the invention, the width and height of the enlarged shaped and sized center section will depend on the size and location of the edentulous space or spaces within the dental arch where a pontic or pontics is replacing missing teeth in a patient's mouth.

Additionally, the occlusal surface of the shaped and sized center section may also have a centrally disposed depression, insert or hollowed out portion so that in the formation of the pontic or pontics on the multi-section infrastructure, composite deposited or formed on the associated occlusal surface of the formed pontic will have an extra thickness at the point where it meets the opposing cusp of the opposite upper or lower teeth particularly during a chewing function so that such thicker or heavier composite is better able to withstand pressure exerted on such pontic or pontics during mastication, clenching of the jaws and nocturnal grinding of the teeth.

The secondary support section is operatively connected to the enlarged shaped and sized center section of the main support bar. In the illustrated embodiments of the multi-section infrastructure, it consists of coacting and associated buccal and lingual side buttresses, so connected in the main support bar that it enables the improved dental prosthesis formed from such multi-section infrastructure in accordance with the present invention to be affixed into suitable shaped cuts in the occlusal surface and into indentations in the mesial-buccal and distal buccal and mesial-lingual and distal lingual proximal sides of the tooth or teeth adjacent to the edentulous space in which the pontic or pontic will be mounted or positioned. This three-point contact arrangement provides an extremely important anti-torque component to the dental prosthesis which prevents rotation around the longitudinal or mesial-distal axis of the dental prosthesis in assembled position.

In another aspect, the secondary support section is operatively connected to the enlarged shaped and sized center section of the main support bar by a buccal groove and a lingual groove which are associated and coact to receive the respective buccal and lingual side buttresses. The buccal groove and lingual groove respectively have a superior border and an inferior border in spaced relation to each other, and the borders are either parallel to each other and relative to the occlusal surface or longitudinal line of the given dental prosthesis.

It is another aspect of the secondary support section that the superior border and inferior border of the respective buccal groove and lingual groove formed on opposite sides of the enlarged shaped and sized center section of the main support bar may also be disposed at an angle to the occlusal surface of the center section or to the longitudinal line of the given dental prosthesis. Further, these borders are either parallel to each other, or the inferior border may diverge to establish a smaller or wider spaced relation between the superior and inferior borders as may be required to adjust the buccal buttress and lingual buttress when the dental prosthesis is connected into assembled position to replace the tooth or teeth in the edentulous space in the patient's mouth.

Additionally, in another aspect of the improved multi-section infrastructure for forming a dental prosthesis in accordance with the present invention, a U-shaped pontic clip can be connected to the enlarged shaped center section of the main support bar to permit relative occluso-gingival adjustability of the main support bar in the preparations in the occlusal surfaces of the tooth or teeth adjacent to the edentulous space so the polished bottom of the U-shaped pontic clip in assembled position in the formed dental prosthesis will rest on the gingival surface of the gums in the edentulous space.

Additionally, in another and still further aspect of the improved multi-section infrastructure for forming a dental prosthesis in accordance with the present invention, the multi-section infrastructure consists generally of a longitudinally extending main support bar having, a shaped and sized center section, at least one connecting end or oppositely projecting connecting ends for connecting the main support bar into the prepared occlusal surface or surfaces in the tooth or teeth adjacent to the edentulous space so the shaped and sized center section can be centered in the edentulous space, a U-shaped pontic clip can be connected to the shaped and sized center section of the main support bar to permit occluso-gingival adaptability of the main support bar relative the preparations in the occlusal surface or surfaces in the tooth or teeth adjacent to the edentulous space so the polished bottom of the U-shaped pontic clip will rest on the gingival surface of the gum in the edentulous space, and the combination thereof with a secondary support means connected to the shaped and sized center section to provide an anti-torque component to the dental prosthesis formed from such multi-section infrastructure.

Various embodiments for achieving these improved multi-section infrastructure for forming a dental prosthesis in accordance with the present invention are hereinafter described.

The present invention also provides the Dentist with at least two improved and optional general methods for structuring, forming and fabricating such dental prosthesis for filling the edentulous space in a given patient's mouth. The first consists of an "in situ" technique which is performed directly in the patient's mouth. The second is an indirect method exterior of the patient's mouth performed on a model of the edentulous space and the adjacent supporting tooth or teeth of the given patient.

Additionally, in another and still further aspect of the improved indirect method for forming a dental prosthesis exterior of the patient's mouth, the use of removable "shims" or "spacers" to prevent cement or composite from filling the buccal and lingual grooves and the transverse connecting pin holes is used during the formation of the replacement pontic or pontics from the cement, composite or equally permanent toothlike materials for the preparatory or preliminary dental prostheses to be transferred and fixed in the edentulous space in the patient's mouth.

The use of the various improved multi-section infrastructures and the formation of the pontic replacement thereon by any of these methods in accordance with the present invention enables the Dentist to provide dental prostheses with an anti-torque component and/or an adjustable hygienic base having a pontic or pontics for replacing the lost tooth or teeth in the edentulous space adjacent to a tooth or between teeth in the patient's mouth in a relatively short period of time at a relatively low cost.

SUMMARY AND OBJECTS OF THE INVENTION

Thus, the present invention covers an improved dental prosthesis for replacing a tooth or teeth in an edentulous space in a patient's mouth which has a multi-section infrastructure including, a longitudinally extending main support bar, said main support bar having a shaped and sized center section and at least one connecting means for connecting the main support bar to at least one of the supporting teeth in the patient's mouth adjacent the edentulous space so that the shaped and sized center section is centered in the edentulous space, and secondary support means operatively connected to the enlarged center section to prevent rotation of the main support bar when the formed dental prosthesis is in assembled position in the edentulous space.

In another aspect of the present invention, an improved dental prosthesis for replacing a tooth or teeth in an edentulous space in the patient's mouth includes a multi-section infrastructure having, a longitudinally extending main support bar, the main support bar has a shaped and sized center section and at least one connecting means for connecting the main support bar to the at least one supporting tooth in the patient's mouth for centering the shaped and sized center section in the edentulous space, and an adjustable U-shaped pontic clip is connectable to the shaped and sized center section of the main support bar to permit occluso-gingival adjustability of the main support bar relative the preparations in the occlusal surfaces of the tooth or teeth adjacent to the edentulous space so the polished bottom of the U-shaped pontic clip in assembled position in the formed dental prosthesis rests on the gingival surface of the gum in the edentulous space.

In still another aspect of the improved dental prosthesis for replacing a tooth or teeth in an edentulous space in the patient's mouth, a multi-section infrastructure includes, a longitudinally extending main support bar having a shaped and sized center section and at least one connecting means for connecting the main support bar to the at least one supporting tooth in the patient's mouth for centering the shaped and sized center section in the edentulous space, an adjustable U-shaped clip with a highly polished base for hygienic purposes is slidably connectable to the shaped and sized center section for adjustably positioning the dental prosthesis in assembled position in the edentulous space to relate the occlusal surface of the gingiva in the edentulous space to the occlusal surface of the main support bar when in assembled position and secondary support means operatively connected to the shaped and sized center section to prevent rotation of the multi-section infrastructure when the formed dental prosthesis is in assembled position in the edentulous space.

Accordingly, it is an object of the present invention to provide an improved dental prosthesis and method for replacing a pontic or pontics in an edentulous space adjacent to a tooth or between teeth in a patient's mouth which can be simply and accurately adjusted and on which the replacement pontic or pontics can be fabricated by the Dentist either "in situ" or exteriorly on a stone cast model of the edentulous space and the adjacent existing prepared teeth in the patient's mouth.

It is another object of the present invention to provide an "in situ" or direct method for assembling, fitting and finishing an improved multi-section infrastructure in an edentulous space in a patient's mouth to form a dental prosthesis having at least one pontic thereon for replacing a tooth or teeth in the edentulous space in the patient's mouth.

It is still another object of the present invention to provide an indirect method utilizing a cast model of the edentulous space in the patient's mouth, at a point exterior of the patient's mouth, for assembling, fitting and preliminarily finishing the tooth or teeth formed from cement, composite or similar hard, toothlike polymeric materials on the improved multi-section infrastructure which can then be moved and fitted directly into the edentulous space in the patient's mouth and finished in assembled position therein.

It is a still further object of the present invention to provide in an indirect method utilizing a cast model of the edentulous space in the patient's mouth, at a point exterior thereof, "shims or spacers" for preventing cement or composite from filling the buccal and lingual grooves and the transverse connecting pin holes during the fabrication of the preparatory or preliminary dental prosthesis before it is transferred to assemble and fix the dental prosthesis in the patient's mouth.

The above and other objects, features and advantages will become apparent from the detailed description of the invention which follows when read in conjunction with the accompanying drawings in which:

BRIEF DESCRIPTION OF THE DRAWINGS

FIG. 22 is a perspective view of the shaped and sized main support bar for the multi-section infrastructure of the dental prosthesis shown in FIG. 18, FIG. 23 is a top plan view of the shaped and sized main support bar for the multi-section infrastructure of the dental prosthesis shown in FIG. 18, FIG. 23A is an enlarged plan view of a fragment of the occlusal surface of the main support bar for the multi-section infrastructure shown at FIG. 18, showing the porosity created by acid etching, sand blasting or other means to rough the exterior surface of such main support bar and other elements of the multi-section infrastructure, FIG. 24 is a cross-section taken on line 24—24 of FIG. 23, FIG. 25 is a cross-section taken on line 25—25 of FIG. 23, FIG. 25A is an enlarged side elevational view of a fragment of the occlusal surface of the main support bar for the multi-section infrastructure shown at FIG. 18 showing the porosity created by acid etching, sand blasting or other means to roughen the exterior surface of the main support bar and other elements of such multi-section infrastructure, FIG. 26 is a perspective view of the form of adjustable U-shaped pontic clip in the multi-section infrastructure for a dental prosthesis as shown in FIG. 18, FIG. 27 is a side view of the U-shaped pontic clip shown in FIGS. 18 and 26, FIG. 28 is a front view of the U-shaped pontic clip shown in FIGS. 18 and 26, FIG. 29 is a top view of the U-shaped pontic clip shown in FIGS. 18 and 26, FIG. 30 is a bottom view of the U-shaped pontic clip shown in FIGS. 18 and 26, FIG. 31 is a cross-section taken on lines 31—31 of FIG. 27, FIG. 32 is an enlarged perspective view of still another embodiment of a multi-section infrastructure for a dental prosthesis in accordance with the present invention having an asymmetrical main support bar and adapted for use with another form of the U-shaped adjustable pontic clip and having positionable buccal and lingual side buttresses, also shown in exploded view in the phantomized lines, FIG. 33 is a top plan view of the multi-section infrastructure for a dental prosthesis as shown in FIG. 32, FIG. 34 is a front end view of the multi-section infrastructure for a dental prosthesis as shown in FIGS. 32 and 33, FIG. 35 is a back end view of the multi-section infrastructure for a dental prosthesis as shown in FIGS. 32 and 33, FIG. 36 is a top plan view of just the shaped main support section of the multi-section infrastructure for a dental prosthesis as shown in FIGS. 32 and 33, FIG. 37 is a side elevational view of just the shaped main support section of the multi-section infrastructure for the dental prosthesis as shown in FIGS. 32, 33 and 36 with the buccal buttress and the pontic clip removed to show the shaped transverse bore and the trapezoidal buccal guide for the buccal buttress, FIG. 43 is a perspective view of another form of the U-shaped pontic clip for a multi-section infrastructure for a dental prosthesis as shown in FIG. 32, FIG. 43A is a plan view of a shaped and sized metallic blank from which the U-shaped pontic clip shown in FIG. 43 is formed, FIG. 44 is a side view of the U-shaped pontic clip shown in FIG. 43, FIG. 45 is a front view of the U-shaped pontic clip shown in FIG. 43, FIG. 46 is a top view of the U-shaped pontic clip shown in FIG. 43, FIG. 47 is a bottom view of the U-shaped pontic clip shown in FIG. 43, FIG. 48 is a cross-section taken on lines 48—48 of FIG. 44.

DETAILED DESCRIPTION OF ONE EMBODIMENT

Figure 1:
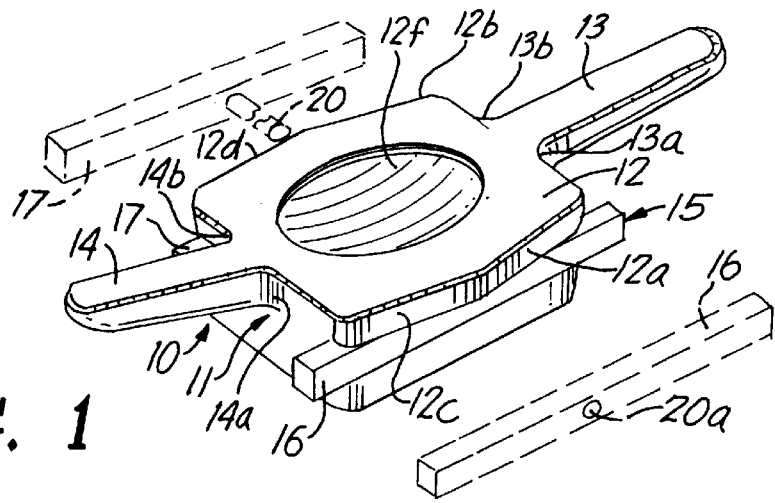
FIG. 1 is a perspective view of one embodiment of a multi-section infrastructure or assembly for a dental prosthesis in accordance with the present invention with the respective side buttresses also in exploded view as shown by the phantomized lines.
Figure 2:
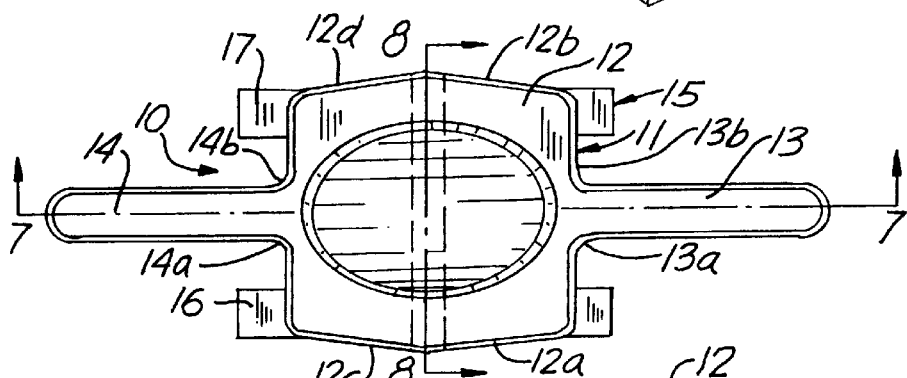
FIG. 2 is a top plan view of the multi-section infrastructure or assembly for a dental prosthesis shown in FIG. 1.
Figure 3:
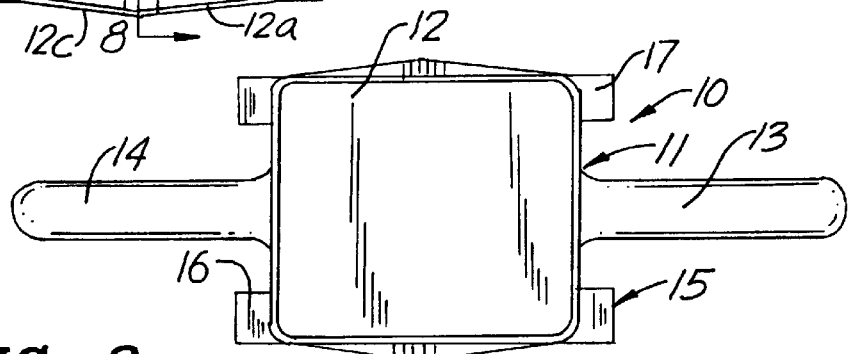
FIG. 3 is a bottom plan view of the multi-section infrastructure or assembly for a dental prosthesis shown in FIG. 1.
Figure 4:
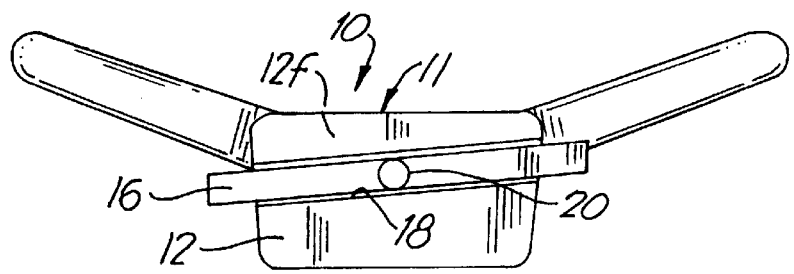
FIG. 4 is a side elevational view of the multi-section infrastructure or assembly for a dental prosthesis shown in FIG. 1.
Figure 5:
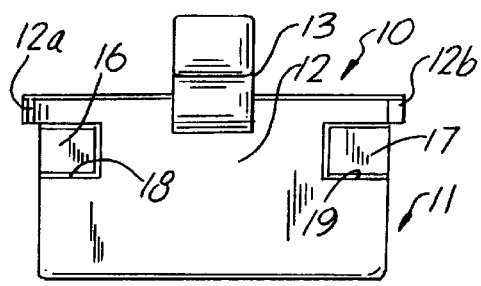
FIG. 5 is a front end view of the multi-section infrastructure or assembly for a dental prosthesis shown in FIGS. 1, 2, 3 and 4.
Figure 6:
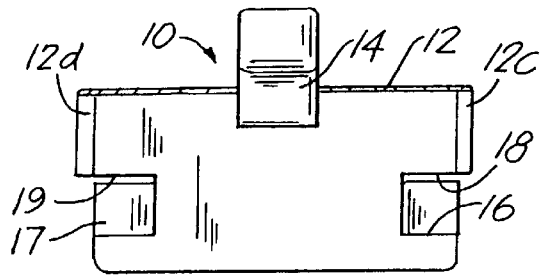
FIG. 6 is a back end view of the multi-section infrastructure or assembly for a dental prosthesis shown in FIGS. 1, 2, 3 and 4.
Figure 7:
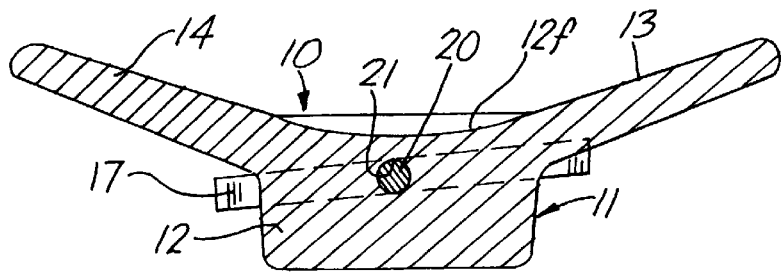
FIG. 7 is a longitudinal cross-section taken on line 7—7 of FIG. 2.
Figure 8:
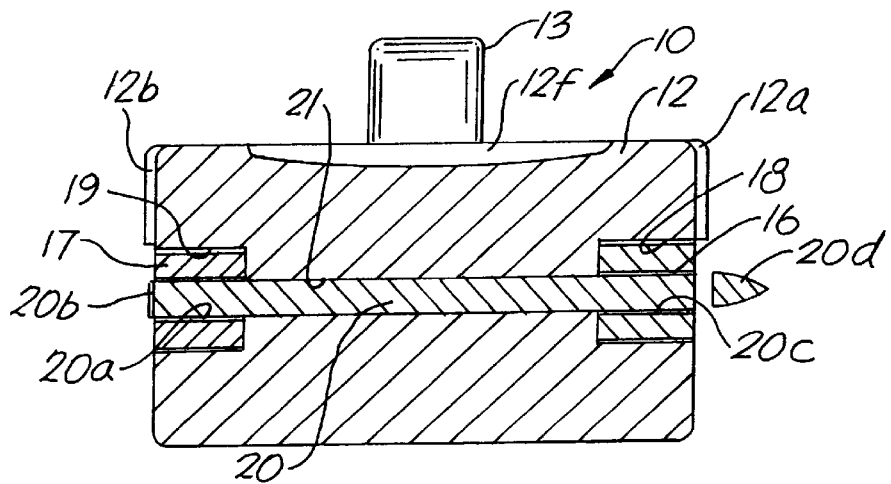
FIG. 8 is a transverse cross-section taken on line 8—8 of FIG. 2.

Referring to the drawings, FIGS. 1 to 8 of the drawings show one form of multi-section infrastructure generally designated 10 for a dental prosthesis in accordance with the present invention, for replacing at least one tooth in an edentulous space in a patient's mouth where the edentulous space is located between a first tooth at the anterior end and a second tooth at the posterior end of the edentulous space.

The multi-section infrastructure 10 consists of a main support bar or beam generally designated 11 having, an enlarged center section 12, and continuous therewith an anterior connecting end 13 or ends and a posterior connecting end 14 or ends for connecting the main support section 11 to occlusal preparations in the respective first tooth on the anterior end of the edentulous space and the second tooth on the posterior end of the edentulous space.

While reference has been made to connecting ends, the embodiments of the invention will be illustrated and described in terms of a single member anterior and posterior connecting ends as shown in FIGS. 1 to 8 and other FIGURES of the drawings. This is not by way of limitation because those skilled in the art will readily recognize that where the main support bar or beam 11 has a multi-member or spaced multi-sections on the connecting end that this design can best be used where the tooth width will permit. Under this latter situation, a supplemental or secondary supporting section or assembly coacting with the main support bar or beam, hereinafter more fully described with respect to the invention as disclosed herein, may be eliminated because such multi-member or spaced multi-section connecting end or ends may be sufficient to meet or prevent the effect of torque caused by forces exerted during the use of the dental prosthesis by the patient.

The relatively enlarged shaped and sized center section 12 is commensurate with or is a function of the edentulous space in which a tooth or teeth need to be replaced. In this illustrated embodiment the center section 12 adjacent the occlusal face or table is shaped in plan view from the medial section to the respective anterior and posterior connecting ends 13 and 14 with oppositely extending tapering buccal and lingual sides as at 12a and 12b for the anterior end and 12c and 12d for the posterior end so that the widest part of the central section is along the medial transverse line of the central section 12 and the section narrows generally uniformly in the respective anterior and posterior directions to provide sufficient space for forming the pontic or pontics on the multi-section infrastructure 10.

The anterior connecting end 13 is connected to the anterior end of the central section 12 and the posterior connecting end 14 is connected to the posterior end of the central section 12. Further, at the point where the respective anterior connecting end 13 and posterior connecting end 14 communicate and connect to the central section 12, the central section 12 is rounded as at 13a and 13b at the anterior end and 14a and 14b at the posterior end, all of which is clearly shown in FIGS. 1, 2 and 3 of the drawings.

FIGS. 1 to 8 further show that the occlusal surface of the central section is provided with at least one hollow concave or indented section as at 12f so that in the formation of the pontic or pontics, as the case may be, the corresponding occlusal surface of the pontic or pontics formed in the multi-section infrastructure 10 will have an increased thickness of composite material over the occlusal surface of the center section of the pontic or pontics and thus have the strength and support necessary to coact with the cusps on the opposing teeth.

The tapered side walls, rounded points of communication and the at least one hollow concave or indented section 12f, as above described, illustrate one preferred sized and shaped central section 12 for the main support bar or beam 11 of the multi-section infrastructure 10 because it enables the pontic or pontics formed to withstand the forces exerted with the coacting upper or lower teeth during mastication, clenching of the jaws and during night grinding of the teeth by the patient. However, those skilled in the art will readily recognize that the central section in plan view can have any desired shape such as square, rectangular, oval, trapezoidal or even a customized irregular shape to meet the requirements for a given edentulous space without departing from the scope of the present invention.

Anterior connecting end 13 and posterior connecting end 14 for the main support bar 12 extend respectively in assembled position in opposite directions mesial-distally along and in assembled position in the general longitudinal line of the teeth adjacent to or on opposite ends of the edentulous space in the patient's mouth so they can be connected into suitable occlusal preparations in such tooth or teeth.

While the anterior connecting end 13 and posterior connecting end 14 are shown in generally symmetrical planes, those skilled in the art will find many varied conditions with respect to the supporting teeth that will require that the anterior connecting end 13 and posterior connecting end 14 be disposed in relatively non-symmetrical planes as is illustrated hereinafter in further embodiments of the present invention. The anterior connecting end 13 and posterior connecting end 14 may also be made of a malleable metal or other material which can be shaped by the dentist or laboratory technician as may be required for a particular edentulous space.

Referring further to FIGS. 1 to 8 of the drawings, coacting with and connected to the main support bar or section 11 is a supplementary or secondary supporting section or assembly generally designated 15 which includes a buccal buttress 16 and a lingual buttress 17 respectively positioned on the buccal and lingual side of the shaped and sized center section 12 and so spatially oriented and so connected with the main support bar or beam 11 that in assembled position the secondary support section can also engage the same first and second teeth at the respective anterior and posterior ends of the edentulous space to which the main support bar or beam 11 is connected so as to form three points of contact which act to prevent rotation of the multi-section infrastructure.

The spatial assembly of the main support bar and the supplemental or secondary supporting section to provide three spaced supporting connections for the multi-section infrastructure for the dental prosthesis in accordance with this form of the invention is a significant advance over prior art infrastructure because it serves as an anti-torque mechanism to eliminate or substantially reduce the problem inherent in prior art fixed bridges to rotate during chewing, clenching of the teeth and the night grinding of teeth which are common acts that natural teeth and hence the replacement pontics must be able to withstand.

This broad concept is applicable to all embodiments of the invention which include such secondary supporting means as the buccal and lingual buttresses above described. Some embodiments, however, must vary because of space requirements or absence of structure on the supporting tooth to enable, for example, the lingual buttress to be attached at either or both ends in a given supporting tooth.

Main supporting bar or section 11 for the multi-section infrastructure 10 with its shaped and sized center section 12, the buttresses and any other element is preferably cast out of a suitable metallic material such as a stainless steel alloy, gold alloy, titanium alloy, silver alloy, platinum alloy or other metal alloys which will lend strength to the multi-section infrastructure for the dental prosthesis in accordance with the present invention. Additionally, however, the multi-section infrastructure 10 and all the elements thereof may be made of other materials such as ceramics, composites, plastics or synthetic polymers having adequate physical properties for the purposes and objects of the infrastructure as herein disclosed.

During fabrication of the multi-section infrastructure, the main support bar or section 11 and the buccal buttress 16 and lingual buttress 17 of the supplemental or secondary support section will be subjected to either sandblasting with an appropriate grit of aluminum oxide, acid etching or subjected to similar or other types of treating procedures to create a desirable surface roughness for increasing the bonding surface for proper mechanical or chemical bonding of the composite, ceramic, plastic or polymer material used for forming and shaping the pontic or pontics during formation of the dental prosthesis in accordance with the present invention.

To reduce stress, increase the strength of the various elements of the infrastructure 10 the main support bar or section 11 and the secondary support section 15 will also be subjected to tumbling in any suitable type of tumbling apparatus so that all the side edges will become rounded and all sharp points and edges will be eliminated.

In the illustrated embodiment shown in FIGS. 1 to 8 of the drawings, the length of the shaped and sized center section 12 of the main support bar or beam 11 is dimensioned for the fabrication of a single pontic to replace a single tooth in an edentulous space between two other existing teeth in the posterior section of the teeth in a patient's mouth.

However, it will be understood by those skilled in the art that the length of the enlarged shaped and sized center section 12 will be a function of the size of the edentulous space, and the number of pontics that are needed to replace the tooth or teeth missing in the edentulous space in the patient's mouth. For a single pontic replacement, the average length of an edentulous space will vary between 4 mm and 8 mm, and the block-like center section 12 of main support bar or beam 11 can be easily sized for such limits. For a longer mesial-distal edentulous space where two or more pontics may be needed to fill the edentulous space, the enlarged block-like center section 12 can be modified and/or manufactured with other sizes to meet these requirements.

Further, however, it will also be obvious to those skilled in the art that there will be some average lengths for the block-like center section 12 which can be applicable for almost all patients whether missing one or two teeth and that the overall length of the main support section 11 can be accommodated and varied for a given edentulous space to be filled by grinding the main section or by cutting off a given length of the respective connecting ends 13 and 14 to enable the block-like center section 12 to be positioned and centered relative a given edentulous space during the fabrication of the dental prosthesis in accordance with the methods of the present invention.

The wide variations of the edentulous space or in the supporting tooth or teeth from patients to patients can be met by providing the Dentist or lab technician forming a dental prosthesis in accordance with the present invention with a kit containing a plurality of the various elements grouped to meet the various average conditions that may be met. By selecting the desired elements, the Dentist or lab technician can customize the multi-section infrastructure as may be necessary to meet the specific requirements of the edentulous space in which a pontic or pontics need to be replaced for a given patient.

By further reference to FIGS. 1 to 8, the respective anterior connecting end 13 and posterior connecting end 14 are shown as disposed in general longitudinal alignment with each other, however, not necessarily in the same generally horizontal plane. This alignment will be a function of the position of the occlusal preparations or cut-outs formed in the occlusal surfaces of the anterior and posterior teeth on the opposite sides of the edentulous space. The enlarged center section 12 in assembled position extends between the respective anterior connecting end 13 and posterior connecting end 14 so that it is more gingival than the generally horizontal plane of the aligned connecting ends 13 and 14. Thus, if the prosthesis being formed is between the teeth in the upper jaw, the occlusal surface of the center section will be higher; conversely, in the lower jaw of the patient's mouth, the occlusal surface of the center section will be lower. This structure for the main support bar or section 11 and the hollow concave or indented section 12f in the occlusal surface of the central section 12 of main support bar 11 will, in the creation, forming and shaping of the pontic or pontics from the cement, composite or similar hard toothlike materials, enable the given pontic or pontics being formed to have a thicker occlusal section or layer of composite thereon which strengthens the highly stressed occlusal surface of the pontic or pontics against damage or failure.

While the occlusal surface of the central section 11 has been shown with an indented section or hollow concave depression as at 12f, for the purposes and objects as above set forth, it will be clear that the occlusal surface may be flat, concave or convex, as may be necessary to customize the given multi-section infrastructure for a given dental prosthesis without departing from the scope of the present invention.

The secondary support section generally designated 15 is established by a longitudinally extending groove 18 on the buccal side and a longitudinally extending groove 19 on the lingual side of the shaped and sized center section 12 in which respectively matching buccal buttress 16 fits into the longitudinally extending buccal groove 18 on the buccal side of the block-like center section 12 and lingual buttress 17 fits into the longitudinally extending lingual groove 19 on the lingual side of the block-like center section 12, all of which is shown in FIGS. 1, 2, 3, 4, 5, 6 and 8 of the drawings.

The respective longitudinally extending buccal groove 18 is further characterized by a first superior border 18a and a first inferior border 18b which are in spaced relation to each other. Similarly, the longitudinally extending lingual groove 19 has a second superior border 19a and a second inferior border 19b which are also in spaced relation to each other. The respective borders act to establish the width of the buccal groove 18 and lingual groove 19 so that the buccal buttress 16 and lingual buttress 17 can be moved as may be necessary when a given dental prosthesis is being assembled in an edentulous space in the patient's mouth.

These respective first and second superior borders 18a and 19a and the respective first and second inferior borders 18b and 19b can also be oriented so that the respective buccal groove 18 and lingual groove 19 will be disposed parallel to or at an angle to the occlusal surface of the center section, and the respective superior and inferior borders may diverge, not necessarily uniformly, to provide a wide variety of spatial uniform widths or non-uniform widths at the anterior and posterior ends of the respective buccal groove 18 and lingual groove 19, all of which is shown in the figures of the various embodiments of the invention as illustrated herein.

In this illustrated embodiment of the invention, the respective buccal groove 18 and lingual groove 19 on the opposite sides of the block-like center section 12 are shown as sloped at an angle to the generally longitudinal occlusal plane for the connecting ends 13 and 14 and the main support bar or beam 11. This is shown because in certain instances the posterior tooth adjacent the edentulous space tilts mesial-gingivally forward much more than the anterior tooth tilts distally, in which case instead of being straight, the respective buccal groove 18 and lingual groove 19 will be sloped to generally parallel the occlusal slope between the respective supporting teeth on the anterior and posterior ends of the edentulous space. Effectively this will dispose the respective anterior and posterior ends of the buccal buttress 16 and lingual buttress 17 for positioning into indentations for the supplemental support assembly in the mesial-proximal of the anterior supporting tooth and distal proximal of the posterior supporting tooth adjacent to the edentulous space in which the pontic or pontics are being used to replace a tooth or teeth in the patient's mouth, as hereinafter more fully described.

Conversely, where no such tilt is present between the anterior tooth and the posterior tooth, the respective buccal groove and lingual groove may be straight or horizontal to generally parallel the longitudinal occlusal plane or surface of the main support bar or beam 11 and its associated anterior connecting end 13 and posterior connecting 14.

Further, when the dental prosthesis is in assembled position, the mesial and distal ends of the respective buccal buttress 16 and lingual buttress 17 will in assembled position be so disposed, in the indentations in the respective anterior and posterior supporting teeth to provide good hygienic conditions for the patient in relation to the gingiva at the patient's gum line.

When the buccal buttress 16 and lingual buttress 17 are disposed in assembled position, the secondary support section 15 will serve to further strengthen the multi-section infrastructure of the dental prosthesis in accordance with the present invention by providing therewith a three point contact, which assembly acts to prevent or limit rotation or torque of the pontic or pontics around the longitudinal axis of the main support bar or beam 11.

When the main support bar or beam is fitted into the occlusal grooves prepared in the respective anterior and posterior teeth on the mesial and distal sides of the edentulous space, the buccal buttress 16 and lingual buttress 17 must be spatially oriented and adjusted for length by grinding or cutting off portions thereof on the respective anterior or posterior ends so that their respective opposite ends can be adapted to fit into the operatively associated indentations in the adjacent mesial and distal proximal surfaces of these same teeth as will be more fully illustrated and described hereinafter in the methods for forming the dental prosthesis in accordance with the present invention.

In order to hold the buccal buttress 16 and lingual buttress 17 in assembled position, the lingual buttress 17 is preferably formed integrally with a connecting pin 20 which extends through a lingual connecting pin opening 20a in the lingual buttress 16 and has a head as at 20b which is swedged to fix the connecting pin 20 at one end in the lingual buttress 17. Thus, when the lingual buttress 17 is positioned in the lingual groove 19, the connecting pin 20 extends through a bore 21 in the center section 12 transversely or generally normal to the longitudinal line of the main support bar or beam 11 and into and through a buccal connecting pin opening 20c in the buccal buttress 16 positioned in the buccal groove 18. Connecting pin 20 will have a length greater than the thickness or width of the shaped and sized central section 12 and will have at its tip a conical end shape to facilitate assembly through the buccal connecting pin opening 20c so that a portion thereof as at 20d can be ground or snapped off to the desired length for purposes of this assembly. The buccal connecting pin opening 20c has a larger diameter than the connecting pin 20 so that it easily passes through this opening. The buccal buttress 16 and the connecting pin 20 will be held in this assembled position by the composite during formation of the pontic on the multi-section infrastructure 10 of the dental prosthesis.

While the connecting pin 20 has been described as integral with the lingual buttress, it will be readily apparent to those skilled in the art that the connecting pin 20 can be made integral with the buccal buttress or be an independent member connectable to the respective buccal and lingual buttresses without departing from the scope of the present invention.

However, in the description hereinafter on the method of forming the dental prosthesis, it will be clear that in the assembly and positioning of the multi-section infrastructure, it will be easier and simpler for the dentist to first assemble the lingual buttress 17 and thereafter connect the buccal buttress 16 into assembled position because it is easier for the dentist to access the buccal side of the patient's teeth than the lingual side.

OTHER EMBODIMENTS OF THE MULTI-SECTION INFRASTRUCTURE

In order to further overcome or prevent rotational conditions from arising in the use of the dental prosthesis 10 in accordance with the present invention, various modifications of the multi-section infrastructure are illustrated.

Figure 9:
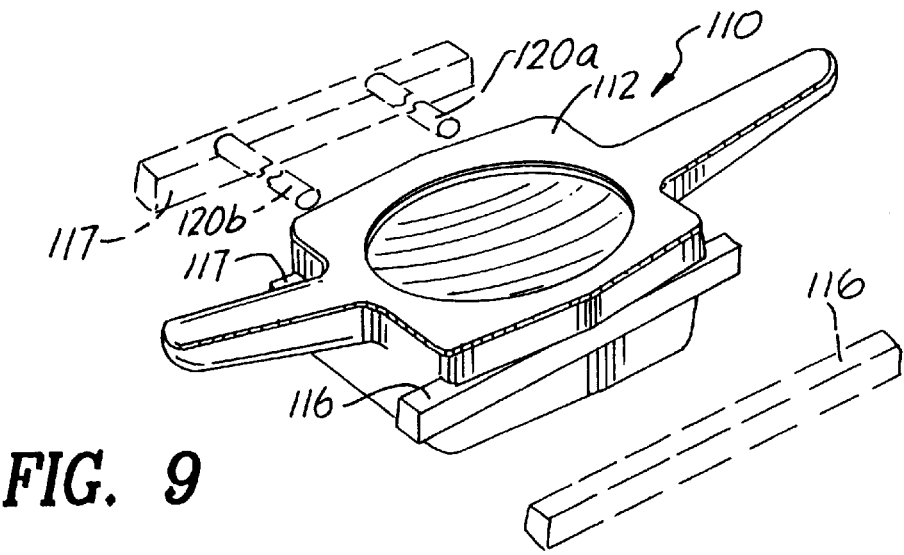
FIG. 9 is a perspective view of another embodiment of the multi-section infrastructure for a dental prosthesis in accordance with the present invention which differs from the multi-section infrastructure shown in FIGS. 1 to 8, by reason of two spaced connecting pins for connecting the respective side buttresses shown in exploded view by the phantomized lines into assembled position.
Figure 10:
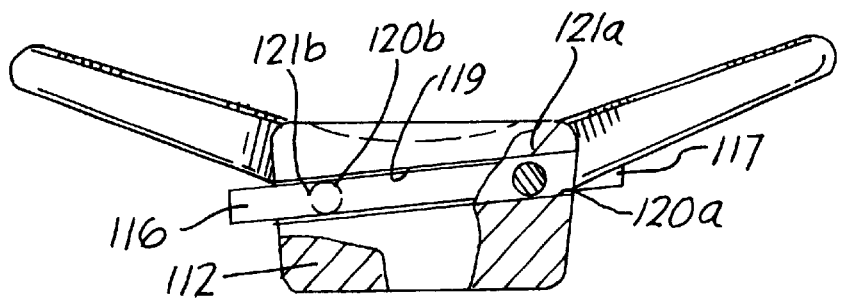
FIG. 10 is a side elevational view of the embodiment of the multi-section infrastructure shown in FIG. 9 partly broken away in vertical section.

Thus, FIGS. 9 and 10 show a multi-section infrastructure 110 for a dental prosthesis in accordance with the present invention wherein the lingual buttress 117 has two spaced connecting pins as at 120a and 120b disposed to extend through mating bores, 121a and 121b in the enlarged block-like center section 112 for contact and operative connection with the buccal buttress 116. This further serves to limit rotation of the respective buccal buttress and lingual buttress in assembled position.

The multi-section infrastructure 110 is otherwise identical to the form of the invention shown in FIGS. 1 to 8 of the drawings and above described and also can be used to fabricate a dental prosthesis in accordance with the present invention.

Figure 11:
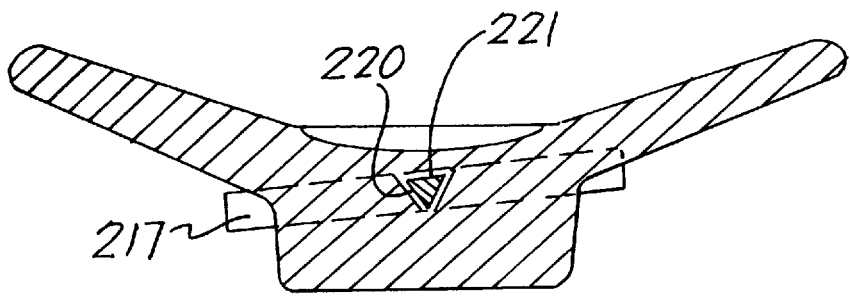
FIG. 11 is a cross-section of another embodiment of the multi-section infrastructure which is similar to the cross-section shown at FIG. 7 and shows one geometric shape for the connecting pin for the side buttresses.

FIG. 11 shows another form of the multi-section infrastructure for a dental prosthesis in accordance with the present invention to overcome any rotational effect during the use of the dental prosthesis in which the transversely disposed connecting pin 220 has some form of geometric shape such as a triangle which fits in a corresponding triangularly shaped transverse bore as at 221. This is another mechanism which serves to limit rotation of the respective buccal buttress and lingual buttress in assembled position.

This form of the invention is otherwise identical with the form of the invention shown in FIGS. 1 to 8 of the drawings and above described and therefore also can be used to fabricate a dental prosthesis in accordance with the present invention.

Figure 12:
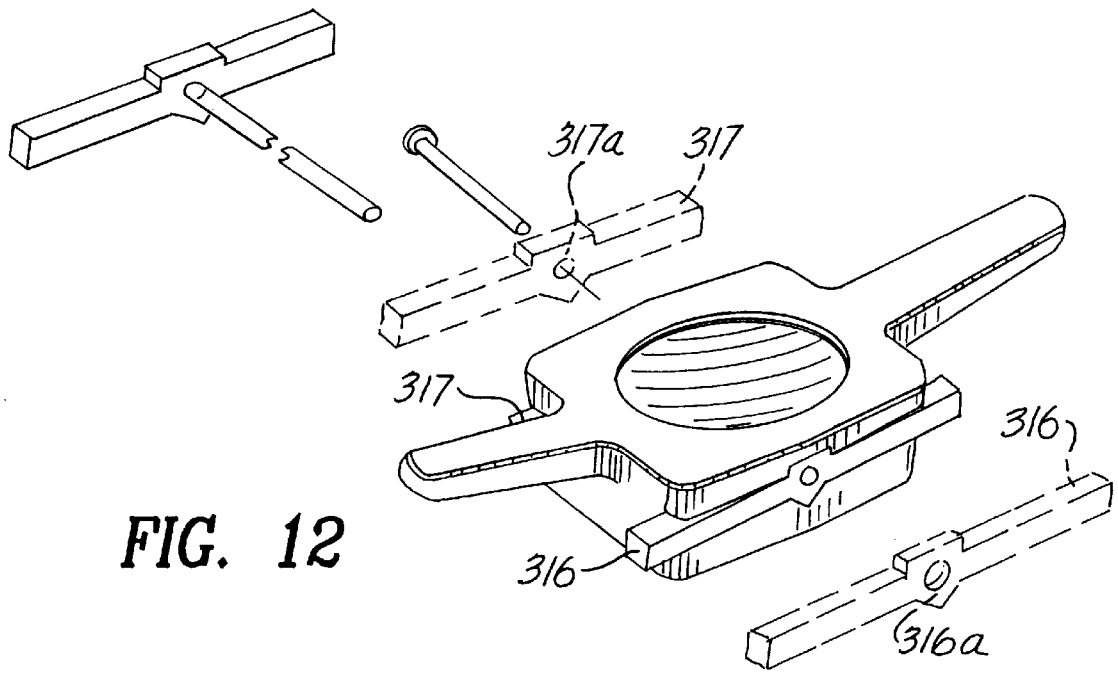
FIG. 12 is a perspective view of another embodiment of the multi-section infrastructure for a dental prosthesis in accordance with the present invention with the respective side buttresses exploded as shown by the phantomized lines, with means for orienting the respective side buttresses.
Figure 13:
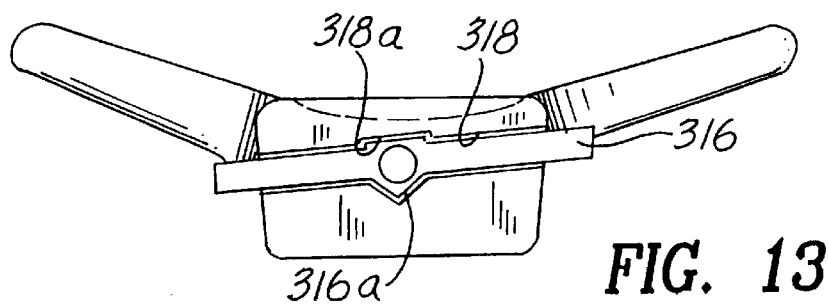
FIG. 13 is a side elevational view of the multi-section infrastructure for a dental prosthesis in accordance with the present invention as shown in FIG. 12.
Figure 14:
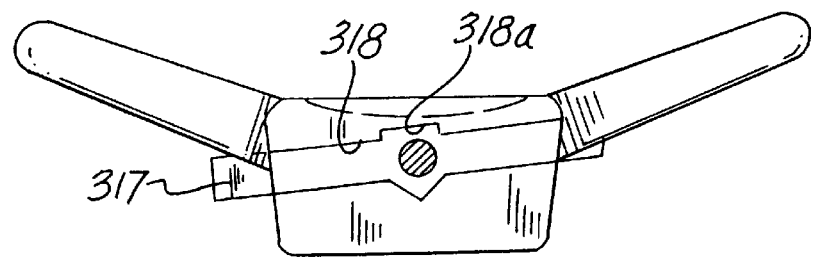
FIG. 14 is a side elevational view of the multi-section infrastructure shown in FIGS. 12 and 13 with the buccal side buttress removed.

In FIGS. 12, 13 and 14 another form of the multi-section infrastructure is shown in which the respective buccal buttress 316 and lingual buttress 317 are modified so that the medial section has a defined asymmetric shape as at 316a for the buccal buttress 316 and 317a for the lingual buttress 317 which fit or engage with a corresponding or mating shaped groove 318a in the central section of the buccal groove 318. A mating shaped groove in the central section of the lingual groove 319, not shown, is similarly provided. Those skilled in the art will recognize that other types of asymmetric shapes may be used, and all such shapes tend to limit rotation of the respective buccal buttress and lingual buttress in assembled position.

This multi-section infrastructure for a dental prosthesis is otherwise identical to the form of the invention shown in FIGS. 1 to 8 of the drawings and above described and can also be used for fabricating the dental prosthesis in accordance with the present invention.

Figure 15:
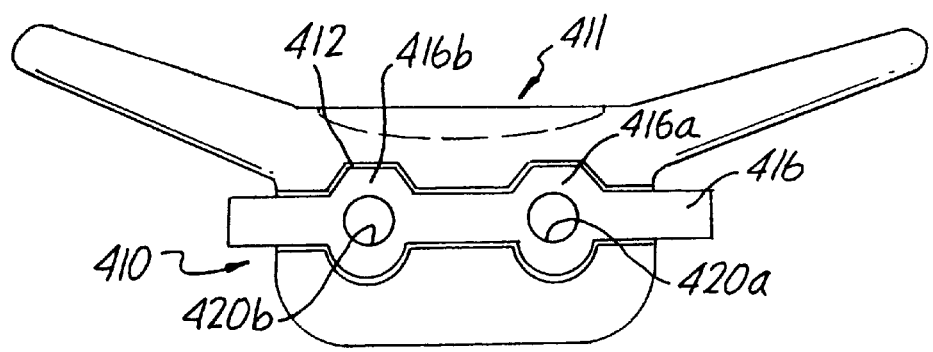
FIG. 15 is a side elevational view of another form of multi-section infrastructure for a dental prosthesis in accordance with the present invention, with another means for orienting the respective side buttresses.
Figure 16:
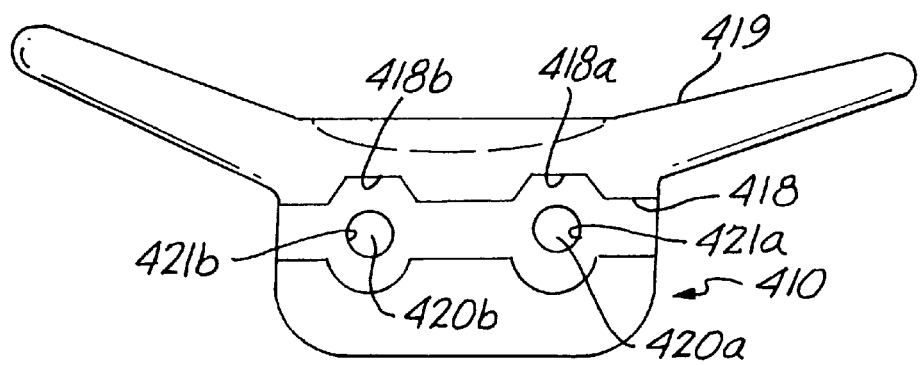
FIG. 16 is a side elevational view of the multi-section infrastructure shown in FIG. 15 with the buccal and lingual side buttresses removed.

FIGS. 15 and 16 show another type of medially spaced and shaped sections for the buccal and lingual buttresses. Only medially spaced and shaped sections 416a and 416b for the buccal buttress 416 are illustrated. This multi-section infrastructure has two spaced connecting pins as at 420a and 420b which extend through transverse bores 421a and 421b. These shaped sections 416a and 416b on the buccal buttress 416 fit into medially spaced mating grooves 418a and 418b as is shown only for the buccal groove 418 in the enlarged block-like center section of the given main support member bar or beam 411 for this form of the multi-section infrastructure 410 for a dental prosthesis in accordance with the present invention.

Figure 17:
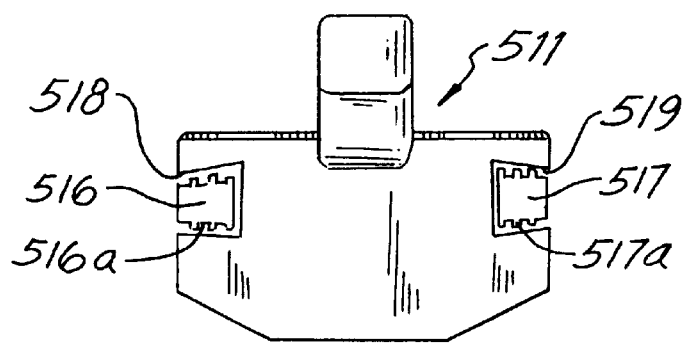
FIG. 17 is a front end view of another embodiment of the multi-section infrastructure showing the buccal and lingual grooves having a keystone shape for holding the buccal buttress and lingual buttress in assembled position without the need for a transverse connecting pin.
Figure 18:
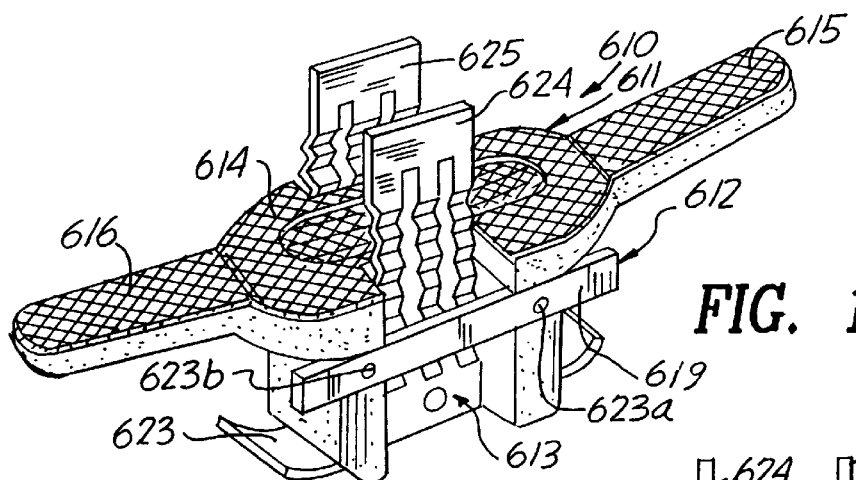
FIG. 18 is a perspective view of another embodiment of a multi-section infrastructure for a dental prosthesis in accordance with the present invention using one embodiment of an adjustable pontic clip.
Figure 19:
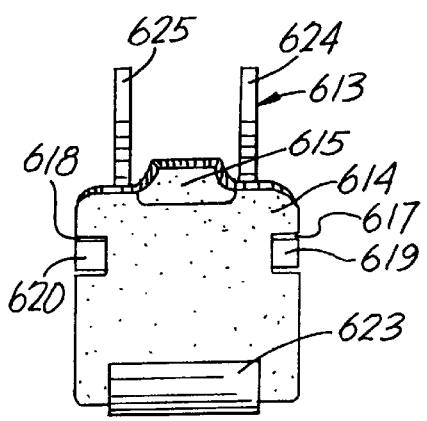
FIG. 19 is a front end view of the multi-section infrastructure for a dental prosthesis shown in FIG. 18.
Figure 20:
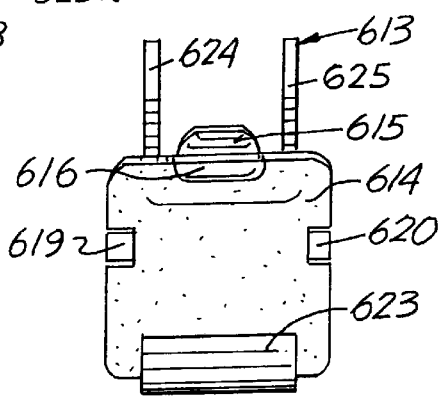
FIG. 20 is a back end view of the multi-section infrastructure for a dental prosthesis shown in FIG. 18.
Figure 21:
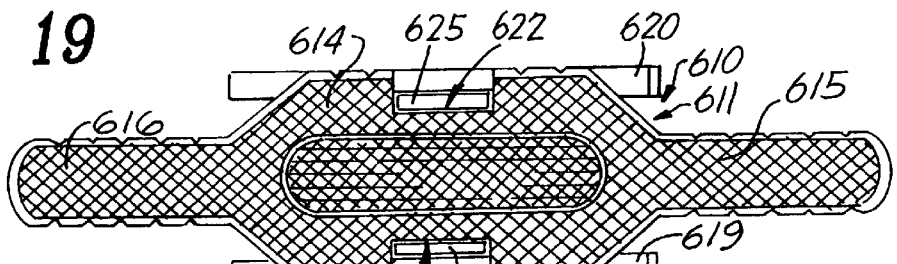
FIG. 21 is a top plan view of the multi-section infrastructure for the dental prosthesis shown in FIG. 18.
Figure 21A:
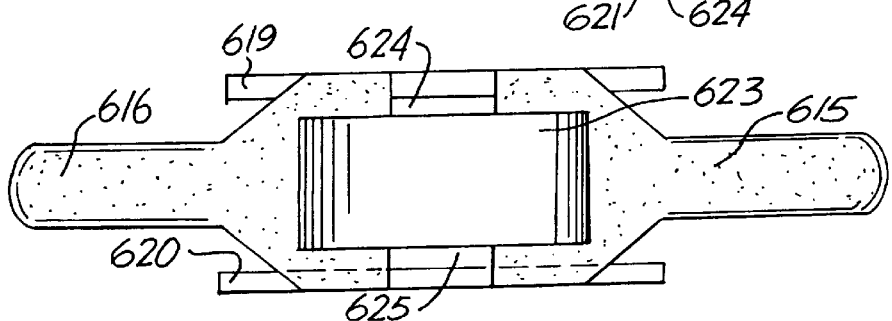
FIG. 21A is a bottom plan view of the multi-section infrastructure for the dental prosthesis shown in FIG. 18.
Figure 38:
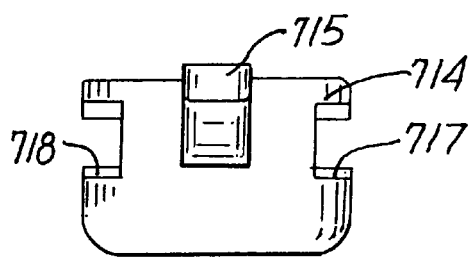
FIG. 38 is a front end view of just the shaped main support section of the multi-section infrastructure for a dental prosthesis as shown in FIGS. 32, 33 and 36.
Figure 39:
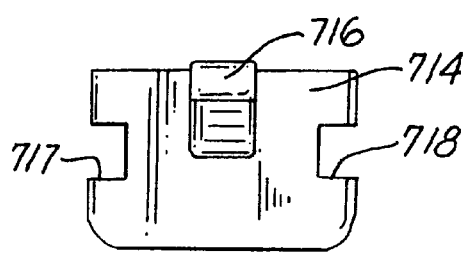
FIG. 39 is a back end view of just the shaped main support section of the multi-section infrastructure for the dental prosthesis as shown in FIGS. 32, 33 and 36.
Figure 40:
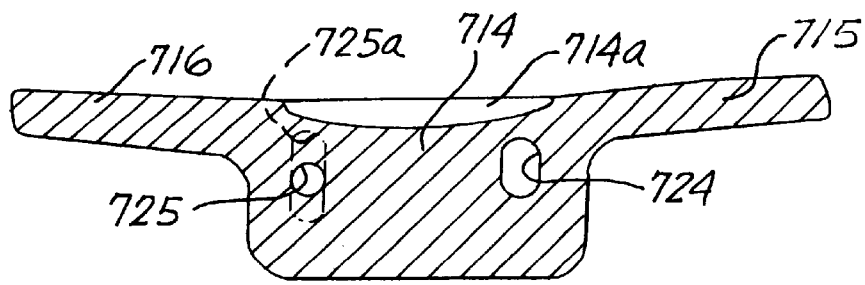
FIG. 40 is a cross-section of just the shaped main support section taken on line 40—40 of FIG. 36, showing variations for the size and shape of the posterior transverse bore in dotted lines.
Figure 41:
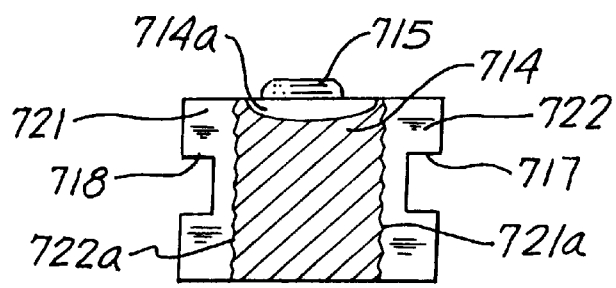
FIG. 41 is a cross-section of just the shaped main support section taken on line 41—41 of FIG. 36.
Figure 42:
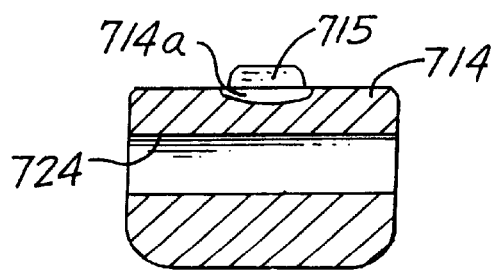
FIG. 42 is a cross-section of just the shaped main support section taken on line 42—42 of FIG. 36.
Figure 49:
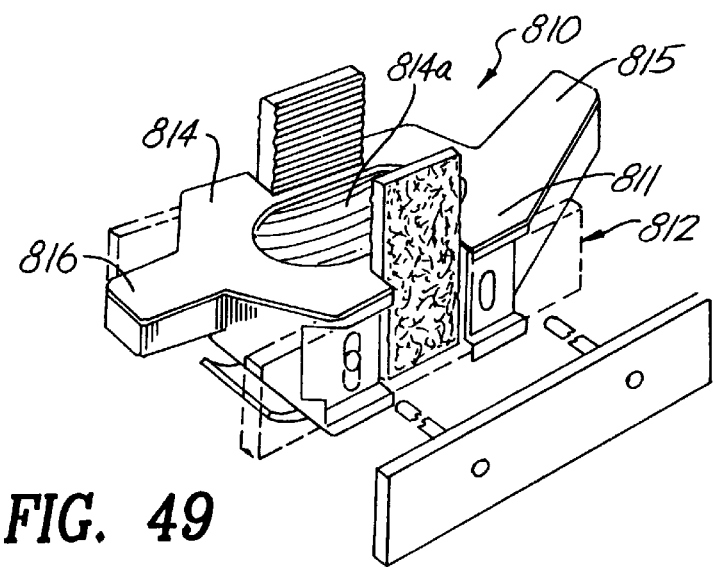
FIG. 49 is an enlarged perspective view of still another embodiment of a multi-section infrastructure for a dental prosthesis in accordance with the present invention having an asymmetrical main support bar adapted for use with a U-shaped adjustable pontic clip and showing only a full buccal side buttress and partially sized lingual side buttresses in phantomized lines and exploded in solid lines.
Figure 50:
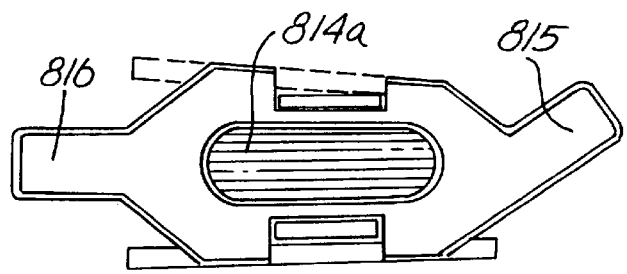
FIG. 50 is a top plan view of the multi-section infrastructure for a dental prosthesis as shown in FIG. 49, showing the interrelation, if any, between the lingual buttress and the anterior connecting end.
Figure 51:
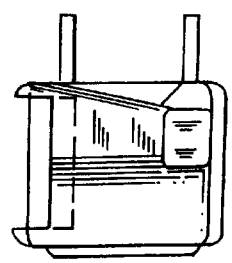
FIG. 51 is a front end view of the multi-section infrastructure for a dental prosthesis as shown in FIGS. 49 and 50.
Figure 52:
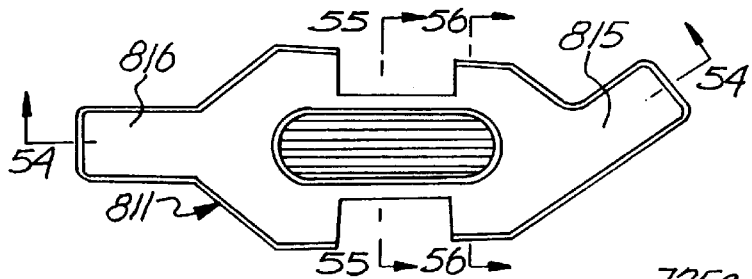
FIG. 52 is a top plan view of just the shaped main support section of the multi-section infrastructure for a dental prosthesis as shown in FIGS. 49 and 50.
Figure 53:
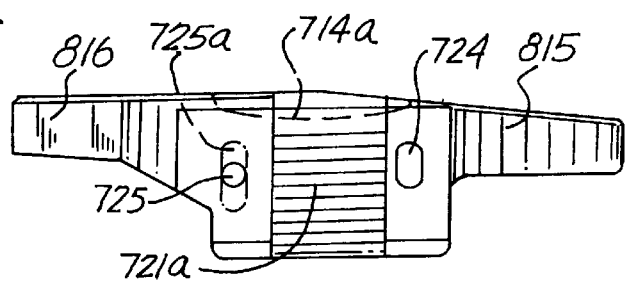
FIG. 53 is a side elevational view of just the shaped main support section of the multi-section infrastructure for the dental prosthesis as shown in FIGS. 49, 50 and 52 with the lingual buttress and the pontic clip removed to show the shaped transverse bore.
Figure 54:
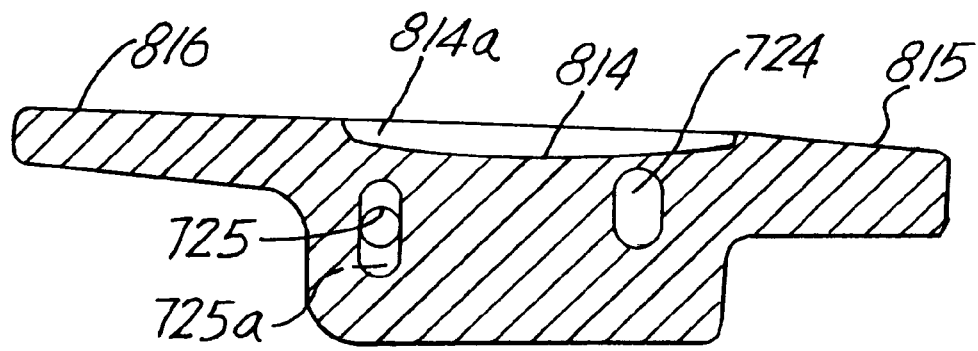
FIG. 54 is a cross-section of just the shaped main support section taken on line 54—54 of FIG. 52.
Figure 55:
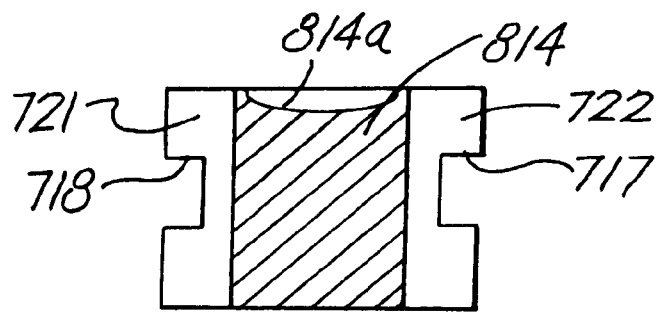
FIG. 55 is a cross-section of just the shaped main support section taken on line 55—55 of FIG. 52.
Figure 56:
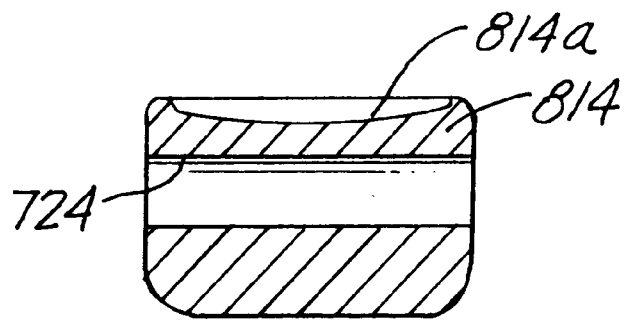
FIG. 56 is a cross-section of just the shaped main support section taken on line 56—56 of FIG. 52.
Figure 57:
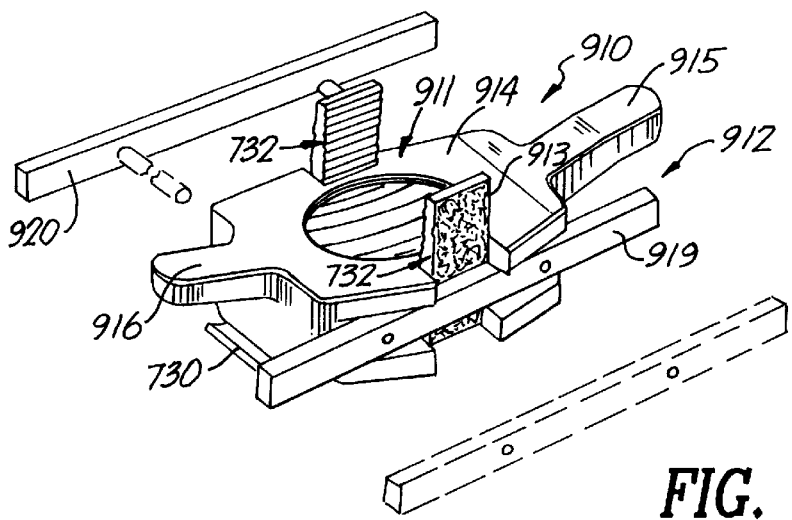
FIG. 57 is an enlarged perspective view of another embodiment of a multi-section infrastructure for forming a dental prosthesis in accordance with the present invention showing a modified form of the shaped and sized main support bar.
Figure 58:
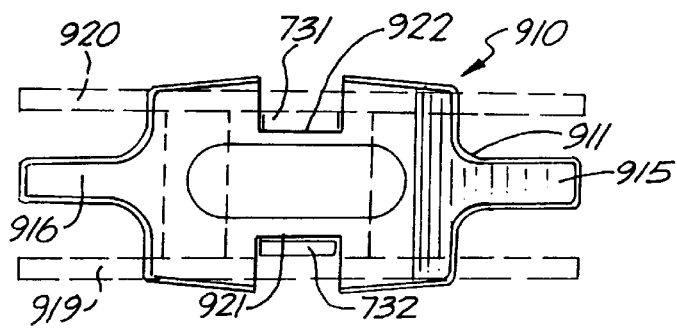
FIG. 58 is a top plan view of the embodiment shown in FIG. 57.
Figure 59:
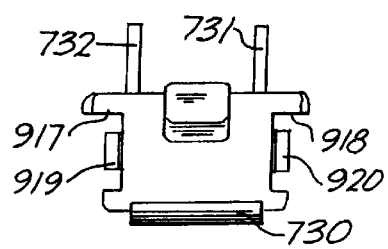
FIG. 59 is a front end view of the multi-section infrastructure for a dental prosthesis as shown in FIGS. 57 and 58.

FIG. 17 shows a still further modification for a multi-section infrastructure generally designated 511 which, as shown in this front end view, have the respective buccal groove 518 and lingual groove 519 with a keystone shape. The associated buccal buttress 516 and lingual buttress 517, if properly sized, may also be either keystone shaped or as shown generally rectangular in cross section with longitudinally extending grooves as at 516a on the buccal buttress 516 and 517a on the lingual buttress 517. The buccal buttress and lingual buttress, however, must be sized to fit through the narrower opening defined by the keystone shape of the buccal groove 518 and lingual groove 519 and are held in assembled position when the composite which is placed into the respective buccal groove and lingual groove and hardens during the formation of the dental prosthesis. This construction enables the buccal buttress 516 and lingual buttress 517 to remain in assembled position without the use of a transverse connecting pin as described for the earlier forms of the multi-section infrastructure shown in FIGS. 1 to 8 and FIGS. 9, 10, 11, 12, 13, 14, 15 and 16 of the drawings.

STILL ANOTHER EMBODIMENT OF THE INVENTION

Referring to the drawings, FIGS. 18 to 31 illustrate a further embodiment of the invention used when the supporting and existing teeth adjacent the edentulous space have sufficient height generally at least 3½ mm or more above the gingival surface of the gum line for the edentulous space in the patient's mouth which requires the replacement of a tooth or teeth.

This embodiment of the multi-section infrastructure generally designated 610 for a dental prosthesis in accordance with the present invention as in the various embodiments above described, is also illustrated and shown for replacing one or more teeth in an edentulous space in a patient's mouth wherein the edentulous space is located between a first supporting tooth at the anterior end of the edentulous space and a second supporting tooth at the posterior end of the edentulous space.

The height of the respective anterior tooth and the posterior tooth permit preparation and cutting of inserts into their respective occlusal surfaces and into the anterior and posterior proximal surfaces of these same supporting teeth, to enable the multi-section infrastructure 610 for a dental prosthesis in accordance with this embodiment of the invention to be fixed and braced in assembled position.

Thus, the multi-section infrastructure for a dental prosthesis generally designated 610, in accordance with this form of the invention, is an assembly consisting of main support bar or beam 611, and a secondary or supplemental support assembly generally designated 612. In addition, this form of the invention utilizes a pontic clip generally designated 613. The secondary or supplemental assembly 612 may be combined with the main support bar or beam 611 alternatively of or selectively with the pontic clip 613 depending on the size and shape of the edentulous space in which the pontic or pontics need to be replaced.

Main support bar or beam 611 is a generally elongated member which will be fabricated by any suitable cost advantage technique preferably from a suitable metallic material such as a stainless steel alloy, gold alloy, titanium alloy, silver alloy or platinum alloy to lend extra strength to the infrastructure of the dental prosthesis. These identified materials are not by way of limitation as other ceramic, composite or plastic materials with or without fiber reinforcement having the required strength and durability may also be used without departing from the scope of the present invention.

Main support bar 611 includes, a sized and shaped center section 614 and a first connecting end 615 which is connected and continuous with the anterior end of the center section 614 and a second connecting end 616 which is connected and continuous with the posterior end of the center section 614 such that the respective end sections 615 and 616 are in general alignment with each other, extend in the approximate centerline of the main support bar 611 but in opposite directions to provide means for connecting the main support bar into assembled position in the occlusal grooves or inserts prepared in the anterior and posterior teeth adjacent the edentulous space as will be more fully described hereinafter.

The shape of the occlusal surface of the main support bar 611 is only for purposes of illustration. Those skilled in the art will recognize that the occlusal surface may be generally square or may be star shaped as shown in the form of the invention shown in FIGS. 1 to 8 of the drawings or may be oval, rectangular or irregular as may be necessary for the particular conditions for the edentulous space in which missing teeth are being replaced. Further, the occlusal surface for the main support bar 611 may be flat or may have in the medial section of the occlusal surface a hollow concave or sized depression as at 611a which is provided for the same objects and purposes as above described for the hollow or sized depression 12f in the main support bar 11 for the form of the invention shown in FIGS. 1 to 8 of the drawings.

Enlarged center section 614 has a length, width and height somewhat less than the length, width and height of the edentulous space in which the pontic or pontics need to be replaced. It is cut, cast, fabricated or formed with longitudinally extending and straight or sloped buccal and lingual grooves as at 617 and 618 to receive matching and fitted buccal buttress 619 and lingual buttress 620 therein to provide the secondary support assembly 612. Medially positioned vertical grooves as at 621 and 622 on opposite sides of the center section 614 coact with the pontic clip 613 to provide a means for adjusting the height of the occlusal surface of the main support bar 611 and therefore the gingival surface of the formed pontic or pontics in the finished dental prosthesis relative the gingival surface of the gum in the edentulous space. Grooves or roughened areas as at 621a and 622a are formed or machined in the respective surfaces of the vertical grooves 621 and 622, as is shown at FIGS. 22, 23 and 24 of the drawings, transverse to the vertical line of the vertical grooves 621 and 622 and facing respectively buccally and lingually to facilitate retention of the pontic clip during formation of the dental prosthesis.

These grooved or roughened sections increase the surface areas for cementing the inner face of the pontic clip 613 into assembled position during the formation or fabrication of the multi-section infrastructure for this embodiment of the dental prosthesis 610.

Further, FIG. 25 shows in side elevation that the wide center section 614 is formed with a generally concave occlusal surface disposed to curve above or below the plane of the respective spaced and oppositely extending connecting sections 615 and 616 depending on whether the dental prosthesis is being used in the teeth in the upper jaw or the lower jaw of the patient's mouth. This structure, along with the hollow concave or sized depression 611a, will serve to increase the thickness of the tooth material which is formed on the occlusal surface of the pontic or pontics subsequently formed thereon to meet the enormous pressures exerted during mastication, clenching of the jaws, night grinding of the teeth or at any other times, due to coacting of the upper and lower teeth of the patient.

This arcuate wide center section 614 and the respective connecting sections 615 and 616 are sized and dimensioned depending on whether a single pontic or more than one pontic is required for replacing a tooth or teeth in the edentulous space. More particularly, the wide center section will have a length which essentially will be a function of the size of the edentulous space. The respective connecting sections as 615 and 616 may be oversized in length to permit them to be cut back or ground so they can be adjusted as may be necessary to fit the dental prosthesis in accordance with this form of the invention, into assembled position.

The same average parameters for the enlarged center section and length of the main support bar or beam 611 as above set forth for the form of the other embodiments above described are equally applicable to this embodiment of the invention and therefore require no additional explanation.

In the supplemental or secondary support assembly 612, the buccal buttress 619 fits into the longitudinally extending buccal groove 617 on the buccal side of the enlarged center section 614 and a coacting lingual buttress 620 fits into the longitudinally extending lingual groove 618 on the lingual side of the enlarged center section 614. The respective buccal groove 617 and lingual groove 618, as in the earlier embodiments of the multi-section infrastructures for the dental prosthesis in accordance with the present invention, may be sloped at an angle or may be straight and generally parallel depending on the plane of the main support bar 611. Similarly, the length of the buccal buttress 619 and lingual buttress 620, are sized all for the same objects and purposes as above described and set forth for the form of the invention shown in FIGS. 1 to 8 of the drawings. Spaced and transverse connecting pins 623a and 623b fit into corresponding transverse bore 624a and 624b for connecting the lingual buttress 619 and buccal buttress 620 in assembled position.

Referring now to FIGS. 18 and 26 to 31 of the drawings, the pontic clip 613 in accordance with this form of the invention is shown as generally U-shaped in side elevation with a base section 623 and side legs 624 and 625 which extend upwardly from the base section 623 as is shown in FIGS. 18, 26, 27, 28 and 31. The side legs 624 and 625 are so spaced from each other that in assembled position they will snugly engage the vertical buccal and lingual side faces 621 and 622 in the enlarged center section 614 on the main support bar or beam 611 and coact with the respective grooves 621a and 622a on the respective vertical buccal and lingual side faces 621 and 622 therein so they can be cemented into assembled position.

The pontic clip is made preferably from a metal such as stainless steel, titanium, titanium alloy or any biocompatible metal which is FDA approved for use in the commercial marketplace for this purpose to enable the outer and lower face of the base section 623 which rests against the gingival surface of the gum in the edentulous space to be highly polished when the dental prosthesis is in assembled position in the edentulous space in the patient's mouth. A polished metal or the like surface will minimize formation of plaque where the polished metal surface rests against the gingival surface of the gum. The above is not by way of limitation because any ceramic or plastic polymer or other natural or synthetic material which provides the necessary qualities of smoothness to minimize plaque formation can be utilized for this purpose.

Base section 623 may have several different arcuate shapes because the ridge or crest of the gingival surface of the gum in the edentulous space will vary from patient to patient. A computer analysis shows that the various shapes of the ridges or crests of the gingival surface of the gums in an edentulous space running mesial-distally follow generally three or four average curves and the pontic clip can therefore be made with base sections which have three or four different radii to fit these various gingival shapes of the gum line for a given edentulous space when forming the multi-section infrastructure for the dental prosthesis for such space. Those skilled in the art will readily recognize that the base section 623 of the pontic clip 613 can be manufactured of malleable materials that will permit easy modification of the curved contacting surface, if necessary, with ordinary orthodontic pliers.

The base section 623 and the side legs 624 and 625 are so formed that the legs can be manually deformed or compressed to facilitate assembly and bonding of the side legs 624 and 625 into assembled position on the enlarged center section 614 of the main support bar or beam 611 in the formation of the multi-section infrastructure for this form of the dental prosthesis. Legs 624 and 625 preferably have roughened inner flat surfaces as at 626 and 627 so they can be assembled and bonded to the grooved or roughened surfaces 621a and 6222a on the vertical buccal groove 621 and lingual groove 622 in the respective buccal and lingual sides of the wide center section 614 of the main support bar or beam 611.

The respective outer surfaces of the legs 624 and 625 are formed with vertically extending slots as at 628a and 628b in leg 625 and 629a and 629b in leg 624, transversely disposed grooves as at 630a, 630b, 630c, etc. on leg 625 and 631a, 631b, 631c, etc. on leg 624, and the respective opposite side edges are serrated on opposite sides as at 632a and 632b for leg 624 and at 633a and 633b for leg 625. In addition, the pontic clip 613 is provided inwardly of the lower end where the respective legs 624 and 625 are connected to the base section 623 with shaped openings as at 634 in leg 624 and 635 in leg 625.

The grooved or roughened inner and outer surfaces, the longitudinal grooves and shaped openings on the side legs 624 and 625 of pontic clip 613 coacting with the composite all help to hold the pontic clip 613 in position when infrastructure 611 is being used to provide a dental prosthesis in accordance with the present invention.

ANOTHER AND STILL FURTHER EMBODIMENT OF THE INVENTION

This embodiment of the invention as shown at FIGS. 32 to 42 is a still further extension of the form of the invention shown in FIGS. 18 to 31 of the drawings and treats with multi-section infrastructures for a dental prosthesis in accordance with the present invention which meets with one of several types of different conditions at the edentulous space in which a pontic or pontics needs to be replaced.

Thus, for example, the multi-section infrastructure for a dental prosthesis that needs to fill the edentulous space formerly occupied by a molar adjacent to a bicuspid needs to take into account the differences between bucco-lingual width at the anterior or bicuspid end of the edentulous space and the corresponding variation in this width at the posterior or molar end of the edentulous space which can be in a range for such width from about 5.5 mm to 10.5 mm. Additionally, the relative planes of the occlusal surfaces between the supporting tooth at the anterior end of the edentulous space and the supporting tooth at the posterior end of the edentulous space may vary so as to create a sloping angle at which the infrastructure for the dental prosthesis will be connected when in assembled position.

The infrastructure in accordance with this embodiment for the dental prosthesis is modified to meet the requirements for an edentulous space with an asymmetrical range of widths so that it can be fitted into assembled position as is hereinafter more fully described.

Thus, referring to FIGS. 32 to 42 of the drawings, the multi-section infrastructure for this embodiment of a dental prosthesis in accordance with the present invention is generally designated 710 and is shown to include, an elongated sized and shaped main support bar or beam 711, and a supplemental or secondary support assembly generally designated 712. In addition, as in the earlier form of the multi-section infrastructure as shown in FIGS. 18 to 25, the main support bar or beam 711 may coact with a pontic clip 713 for the same objects and purposes and therefore may be used alternatively or selectively with the supplemental or secondary support assembly 712, as has been above described for the form of the invention shown at FIGS. 18 to 25.

The main support bar or beam 711 is a generally elongated member which will be fabricated by any suitable cost advantage technique from a suitable metallic material such as a stainless steel alloy, titanium alloy, silver alloy, gold alloy or platinum alloy to lend extra strength to the infrastructure of the dental prosthesis, or from a ceramic, composite, plastic or synthetic polymer having sufficient strength and durability for this purpose.

Main support bar or beam 711 includes a sized and shaped center section 714, an anterior connecting member 715 which is connected and continuous with the anterior end of center section 714 and a posterior connecting member 716 which is connected and continuous with the posterior end of the center section 714 such that the respective connecting members 715 and 716 extend along the approximate longitudinal line of the main support bar 711 but in opposite directions to provide means for connecting the main support bar 711 into assembled position. When the anterior connecting member 715 and posterior connecting member 716 are properly fitted into assembled position in the prepared teeth adjoining the edentulous space, the enlarged center section 714 will be generally centered in the edentulous space so that the pontic or pontics formed thereon will replace the tooth or teeth missing from the edentulous space.

Sized and shaped center section 714 is asymmetrical in plan view and thus is smaller at the anterior mesial end than at the posterior distal end as is shown by FIGS. 32 and 33 of the drawings. The length, width and height of the enlarged center section 714 is less than the length, width and height of the edentulous space into which the replacement pontic or pontics must be formed and fitted. The enlarged center section is cut or formed with longitudinally extending buccal and lingual grooves as at 717 and 718 to receive matching or mating buccal buttress 719 and lingual buttress 720 to provide the secondary or supplement support assembly 712.

In addition, the enlarged center section 714 has on the respective buccal and lingual sides thereof a medially disposed vertical buccal groove 721 and a medially disposed vertical lingual groove 722. The vertical buccal groove 721 and vertical lingual groove 722 lie in a plane behind the plane for the longitudinally extending buccal side groove 717 and lingual side groove 718 so that the vertical buccal and lingual grooves 721 and 722 can coact with the pontic clip 713, all of which is shown in FIGS. 32, 33, 34 and 36 of the drawings. Those skilled in the art will recognize that the secondary or supplementary assembly 712 and the pontic clip 713 can be used alternately or selectively, either independently of each other or in combination, depending on the particular requirements for a given edentulous space.

In order to enable the multi-section infrastructure 710 in accordance with this embodiment of the dental prosthesis to be properly connected into assembled position, the superior borders 17a and 18a and the inferior borders 17b and 18b of the respective buccal and lingual side grooves 717 and 718 define a trapezoidal shape in side-view and therefore are wider at the anterior end than the posterior end of the enlarged center section 714, as is clearly shown in FIGS. 32 and 37 of the drawings. These trapezoidal shaped buccal side groove 717 and lingual side groove 718 coact with spaced, transverse anterior bore 724 and transverse posterior bore 725, which extend from side to side the full width of the enlarged center section 714, from the buccal side groove 717 to the lingual side groove 718 to enable the buccal buttress 719, to be assembled into the buccal side groove 717 so that the connecting pins 726 and 727 extend through the transversely extending anterior bore 724 and posterior bore 725 for connection by composite or any other suitable means in the spaced bores 728 and 729 in the buccal buttress 720 to hold the respective lingual buttress 720 and buccal buttress 719 in assembled position in the lingual side groove 718 and buccal side groove 717. As in the earlier forms of the invention, the tips of the connecting pins will have a cone shape to facilitate assembly and connection in the spaced bores 728 and 729 in the buccal buttress 719, all of which is shown in FIGS. 32, 33, 34 and 37 of the drawings.

FIG. 37 further shows that the transverse anterior bore 724 has an oval shape and by reason of the trapezoidal shape of the respective buccal side groove 717 and lingual side groove 718 when the buccal buttress 719 and lingual buttress 720 are in assembled position the respective buttresses when connected by connecting pin 726 can slide up and down in the transverse anterior bore 724 so that the respective ends of the buccal and lingual buttresses can be adjusted to enable this embodiment of the multi-section infrastructure to be properly mounted more easily into the indentations in the supporting teeth on the anterior and posterior side of the edentulous space in which the pontic or pontics need to be replaced.

Although the transverse anterior bore 724 is illustrated with an oval hole, those skilled in the art will recognize that the transverse anterior bore 724 may be a round hole having a diameter greater than the associated connecting pin 726 which extends through the transverse anterior bore 724 without departing from the scope of the present invention. Similarly, the transverse posterior bore 725, although illustrated as a round bore, may have a diameter greater than the associated connecting pin 727 or may be oval as shown by the phantomized lines at 725a in FIGS. 37 and 40 of the drawings. Such variations of the transverse anterior and posterior bores 724 and 725 may be desirable to facilitate assembly and fitting of the multi-section infrastructure into assembled position in the edentulous space.

In order to enable the secondary or supplemental assembly 712 and the pontic clips 713 or such other pontic clips as are described herein to be used in combination with the supplemental assembly 712, the enlarged center section must have a sufficient width to permit the respective vertical buccal and lingual grooves 721 and 722 to be cut or so formed as to enable the pontic clips 713 or any of the pontic clips described herein to fit into assembled position in association with the buccal buttress 719 and lingual buttress 720 as is shown in FIGS. 18, 21, 32 and 33 of the drawings.

The simpler but somewhat different pontic clip 713 fits into and coacts with the transverse buccal and lingual grooves 721a and 722a cut and formed in the surfaces of vertical buccal groove 721 and vertical lingual groove 722 in the shaped and sized center section 714 of the main support bar or beam 711 for the form of multi-section infrastructure 710 shown in FIGS. 32 to 42 of the drawings.

FIGS. 43, 43A, 44, 45, 46, 47 and 48 show that pontic clip 713, like pontic clip 613, is generally U-shaped in side elevation with a base section 730 from which side legs 731 and 732 extend upwardly.

Pontic clip 713 will be better understood by reference to FIG. 43A which shows one form of stamping or shaped blank generally designated 713a from which the pontic clip 713 will be formed. On the blank 713a the elongated base 730 has the side legs 731 and 732 connected so that they extend in transversely of the longitudinal legs of the elongated base 730 in opposite directions from each other. Thus, when legs 731 and 732 are bent upwardly from the base 730, they form the U-shaped pontic clip 713. However, at the point where the side legs 731 and 732 intersect, cutouts are provided as at 733a and 733b on the respective opposite sides of the leg 731 and at 734a and 734b on the opposite sides of leg 732. Thus, when the respective side leg 731 and side leg 732 are bent to provide the desired U-shape for pontic clip 713, the side legs 731 and 732 are notably in spaced position with respect to each other, but the respective legs are so positioned that they lie or align with the side edges of the base 723, all of which is clearly shown in FIGS. 43, 43A, 45, 466, 47 and 48 of the drawings.

These figures also show that the side legs 731 and 732 are so spaced from each other that like pontic clip 613, they will in assembled position snugly engage the respective vertical buccal groove and lingual groove 721 and 722 in the shaped and sized central section 714. In addition, these figures show that on the respective inner side faces as at 731a and 732a, the side legs 731 and 732 also have transverse grooves or are roughened transversely with respect to the vertical lines of the respective legs so that during assembly, these grooved or roughened surfaces 731a and 732a can functionally engage the similarly grooved or roughened surfaces 721a and 722a on the buccal face and lingual face of the vertical buccal groove 721 and vertical lingual groove 722 in the shaped and sized central section 714 of the main support bar or beam 711 and thus can form therewith a tight fit when cemented into assembled position.

Pontic clips 613 and 713 will be made of materials which will permit, for example, the legs 732 and 732 of pontic clip 713 to be flexed towards and away from each other to achieve some functional engagement for holding the pontic clip 613 or 713 before it is cemented into assembled position.

Moreover, before either of the pontic clips are connected to and bonded into assembled position on the main support bar 711, the pontic clips are adjusted, so the pontic clip base, for example, base 730 of pontic clip 713, is adjusted so that it touches the gingival tissue or the equivalent occlusal surface of the edentulous space, as hereinafter more fully described. Further, the grooved inner side faces 731a on leg 731 and 732a on leg 732 of, for example, the pontic clip 713, is disposed to functionally engage the respective buccal or roughened inner surface 721a in vertical buccal groove 721 and lingual and roughened inner surface 722a in vertical lingual groove 722, to prevent the given pontic clip from separating or falling off of the main support bar 711 as it is moved into the mouth of the patient, and the main support bar 711 is placed into position for forming the dental prosthesis in accordance with the present invention.

In view of the similarity in shape and size, pontic clip 713 may be utilized in the place and stead of pontic clip 613 and vice versa, with such minor modifications as may be necessary to accomplish the objects and purposes of these respective pontic clips or such others as are shown and described herein, as the conditions for replacing a tooth or teeth in the edentulous space in the patient's mouth may require.

As in the earlier and similar embodiments above described, when the pontic clip 713 is in assembled position, the elongated base 730 will be disposed under the enlarged center section 714 and the respective side legs 731 and 732 will fit and extend upwardly through the associated vertical buccal groove 721 and vertical lingual groove 722, all of which is clearly shown in FIGS. 32 and 33 of the drawings.

To assist in the operative association of the pontic clip 713 with the respective buccal buttress 719 and lingual buttress 720, the side legs 731 and 732 also have their outer surfaces as at 731b and 732b grooved or roughened. As in the pontic clip 613 for the earlier embodiment of the multi-section infrastructure above described, after the pontic clip 713 is bonded to the main support bar 711, these above described elements, such as the grooved or roughened outer surface on the pontic clip 713, improve the bonding and retention of the cementing or composite material for forming the pontic or pontics on the multi-section infrastructure during the formation of the dental prosthesis in accordance with this form of the present invention.

Also, as in the early embodiment above described for the form of the multi-section infrastructure as shown in FIGS. 1 to 8 of the drawings, the main support bar 711, the exterior surfaces of the respective buccal and lingual buttress and the outer surfaces of the pontic clip 713 will be acid etched, sand blasted or surface roughened, to increase their surface area and to improve retention of the cementing or composite material during the fabrication of the pontic or pontics formed on a given dental prosthesis and in the cementing and fixing of the connecting ends 715 and 716 of the main support bar or beam 711 for the dental prosthesis into assembled position in the teeth adjacent to the edentulous space in the patient's mouth in which a tooth or teeth need to be replaced.

While a rectangular main support bar or beam 611 was illustrated for the form of the dental prosthesis shown in FIGS. 18 to 25 and an asymmetrical main support bar or beam 711 was illustrated for the form of the dental prosthesis shown in FIGS. 32 to 37, this is not intended by way of limitation because the main support bar or beam for any of the forms of the dental prosthesis as shown herein may take any other form or shape such as oval, diamond or triangular as may be necessary for the particular conditions which prevail for a given edentulous space adjacent to or between the teeth in the patient's mouth.

STILL ANOTHER AND FURTHER EMBODIMENT OF THE INVENTION

This embodiment of the invention as shown in FIGS. 49 to 56 of the drawings is an extension of the form of the invention shown at FIGS. 32 to 42 of the drawings and therefor treats with a multi-section infrastructure for a dental prosthesis that needs to fill an asymmetrical edentulous space formerly occupied, for example, by a bicuspid or bicuspids adjacent to a cuspid at the point where the teeth form a circle or arch with the teeth at the front end of the patient's mouth. Such infrastructure must not only allow for the differences between the mesial-distal length but also for the differences in the bucco-lingual widths at the anterior bicuspid-cuspid end and the posterior or bicuspid or molar end of the edentulous space, the slope caused by the relative planes of the occlusal surfaces of the spaced anterior and posterior supporting teeth and more particularly the change of the curvature from the respective anterior teeth to the more evenly aligned posterior teeth, either to the right or left as the case may be, and whether in the upper jaw or the lower jaw.

Thus by reference to FIGS. 49, 50, 51, 52, 53, 54, 55 and 56, the multi-section infrastructure generally designated 810 for this embodiment is adapted to meet the requirements for such an asymmetrical edentulous space that is disposed where the teeth in a patient's mouth are on a curve between a supporting anterior cuspid tooth and a supporting posterior bicuspid or molar tooth, as the case may be. Multi-section infrastructure 810 includes a main support bar or beam 811, a supplemental or secondary support assembly generally designated 812 which differs somewhat from the secondary support assemblies above described for reasons that will be clear from the description which follows below and may as in some of the earlier embodiments also have a pontic clip 813 for coaction with the main support bar or beam 811 and the supplemental or secondary assembly 812 for the same objects and purposes as above set forth in these above embodiments of the present invention. Those skilled in the art will readily recognize that either of the pontic clips as at 613 and 713 my be used and further that the supplemental or secondary support assembly at 812 or any of such pontic clips can also be used independently, alternately or selectively of each other depending on the nature and size of the mesial-distal length of the missing tooth or teeth that need to be replaced in the edentulous space.

The main support bar or beam 811 is a generally elongated member which will be fabricated from a suitable metallic material such as a stainless steel alloy, titanium alloy, gold alloy, platinum alloy or any FDA approved material to lend strength to the infrastructure of the dental prosthesis or from a ceramic, composite or plastic having sufficient strength and durability for this purpose.

Main support bar or beam 811 includes a sized and shaped center section 814, and anterior connecting member 815 which is connected and continuous with the anterior end of the center section 814 and a posterior connecting member 816 also connected and continuous with the posterior end of center section 814. A pontic clip as at 813 may also form part of the multi-section infrastructure 810.

This embodiment differs from the earlier forms of the invention above described in that the anterior connecting member 815 extends to the left of the longitudinal line of the main support bar 811 and while the posterior connecting member 816 is illustrated as extending in the opposite direction from the anterior connecting member generally in the longitudinal line of the main support bar 811, if the curvature between the anterior supporting tooth and the posterior supporting tooth respectively adjacent to the edentulous space so require, the posterior connecting member 816 can be formed or bent with a dental pliers to the right or left of the longitudinal line of the main support bar 811 thus enabling the main support bar 811 to be connected into assembled position on the respective teeth adjoining the edentulous space so that the enlarged center section will fit into and be centered in the edentulous space where the pontic or pontics formed thereon will replace the missing teeth.

In this embodiment as in the earlier embodiments, the shaped and sized center section 814 also has in the occlusal surface a hollow concave or indented depression 814a for the same purpose and objects as the hollow concave or indented depressions 611a and 714a above described for the forms of the invention shown at FIGS. 18 to 25 and FIGS. 32 to 42 of the drawings.

Enlarged center section 814 is also asymmetrical in plan view or may have such other shape as may be required by the edentulous space or desired by the dentist for mechanical, aesthetic or other reasons and includes substantially the same members and means for connecting the supplement or secondary support assembly 812 and/or the pontic clip 813 as is shown and above described for the embodiment at FIGS. 32 to 42 of the drawings. However, in this embodiment, it is often necessary to modify the supplemental or secondary supporting assembly 812. First, because the anterior connecting end 815 when turned or curved is offset from the longitudinal line of the sized and shaped center section 814 which reduces, limits or restricts the length of the space available at the lingual side of the center section 814 for the lingual buttress of the secondary supporting assembly 812. Second, where this embodiment is used, in the curved section of the patient's teeth, the cuspids, because of the lingual inclined slope do not have sufficient height and width on the lingual proximals to cut indentations on the lingual side of such cuspids.

Thus, while the embodiment includes and shows the buccal groove 917 and lingual groove 918 similar to such grooves in the earlier embodiments above described, only the buccal buttress 919 is shown in solid lines in assembled position while the lingual buttress 920 is shown in phantomized form with dotted lines. The lingual buttress 920 is illustrated in phantomized form because it must either be eliminated due to the reduction in the space on the lingual side of the center section covered by the curved or turned position of the anterior connecting end 915 or it must be trimmed so that it will not be necessary to position the anterior and/or posterior end in indentations which cannot be provided because of the very small transverse proximals on the cuspid supporting tooth or teeth adjacent to the edentulous space in which the tooth or teeth are being replaced.

The same character numerals, description and statements made above with respect to the earlier embodiment shown at FIGS. 32 to 42 apply equally to the embodiment shown at FIGS. 49 to 56 of the drawings.

A STILL FURTHER EMBODIMENT OF THE INVENTION

In FIGS. 57 to 60, another form of infrastructure generally designated 910 for forming a dental prosthesis in accordance with the present invention is illustrated for use where the depth between the plane of the occlusal surface of the supporting tooth or teeth and the gingiva for the edentulous space is relatively small.

This is effectively met by reducing the height of the central section of the main support bar, making the grooves for the respective buccal and lingual side of the main support bar substantially wider without changing or making the respective buccal and lingual buttresses wider and providing large transverse bores so that when the connecting pins are in assembled position in the associated transverse bores, the respective buccal and lingual buttresses can be freely moved up and down to accommodate where the indentations can be established in the anterior and/or posterior proximal surfaces of the associated support teeth, all of which is more fully described in the methods set forth below for creating the dental prosthesis in accordance with the present invention.

Thus referring to FIGS. 57 to 60 of the drawings, the multi-section infrastructure generally designated 910 for forming a dental prosthesis in accordance with this form of the invention, like the earlier forms of the inventions above described, has a main support bar or beam 911 having a sized and shaped center section 914, a supplemental or secondary support assembly, generally designated 912, and a pontic clip 913 which coacts with the main support bar or beam 911 and the secondary support assembly 912 for the same objects and purposes and in the same manner as above described.

As in the earlier forms of the invention, main support bar 911 will be fabricated by any suitable cost advantage technique from any suitable material such as has been enumerated above with respect to main support bars or beams 611, 711 and 811.

Connected to the respective anterior and posterior ends of the enlarged center section 914 are the anterior connecting end 915 and posterior connecting end 916 which are so connected that they extend along the longitudinal line of the main support bar 911 but in opposite directions and operate and function for connecting the main support bar 911 into assembled position in the prepared occlusal grooves in the teeth adjoining the edentulous space, as above described for the connecting ends 615 and 616 for the form of the invention shown in FIGS. 18 to 31 or connecting ends 715 and 716 for the form of the invention shown in FIGS. 32 to 48 or connecting ends 815 and 816 for the form of the invention shown at FIGS. 49 to 56.

The enlarged center section 914, while shown as generally symmetrical in plan view, may have any other shape consistent with the requirements for the given edentulous space where pontic or pontics need to be replaced. In this illustrated embodiment of the present invention, the generally symmetrical shape in plan view and side view is substantially similar to that above described for the form of the invention shown in FIGS. 1 to 8 of the drawings. Thus, the enlarged center section 914 will be widest at the medial section and will taper generally uniformly so that the shape narrows towards the respective anterior and posterior ends of more particularly the upper section or the occlusal table for center section 914. The length, width and height of the enlarged center section 914 will be a function of the corresponding length, width and height of the edentulous space where the pontic or pontics need to be replaced.

It is thought clear from FIGS. 52 to 60 that the limited width of the center section and its limited height will be particularly ideal for an edentulous space in which the adjacent supporting tooth or teeth are relatively wide but the depth from the occlusal surface of such teeth to the gingiva of the edentulous space is relatively small.

The enlarged center section as in the earlier forms of the infrastructure above described, has the vertical buccal groove 921 and vertical lingual groove 922 into which the legs 931 and 932 of the pontic clip 913 will slidably fit to enable the main support bar 911 to be adjusted relative the edentulous space and the prepared occlusal grooves in the respective teeth adjacent the edentulous space when the polished base section 930 of the U-shaped pontic clip is resting on the occlusal surface of the gingiva or gum line in the edentulous space in the patient's mouth, all of which is shown in FIGS. 57, 58, 59, 60 and 61 of the drawings.

Figure 61:
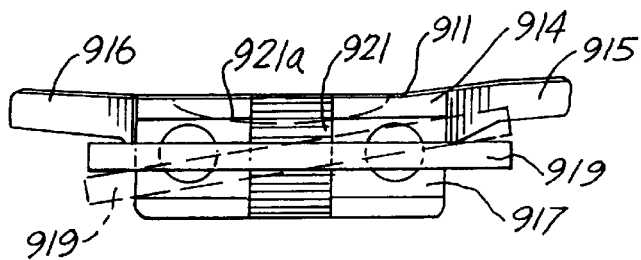
FIG. 61 is a side view of just the main support bar.
Figure 60:
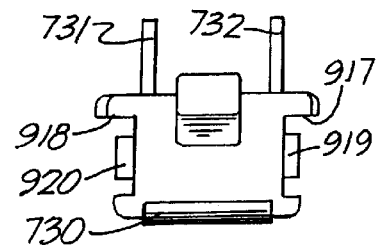
FIG. 60 is a back end view of the main support bar with the pontic clip and the buccal and lingual side buttresses in assembled position.
Figure 62:
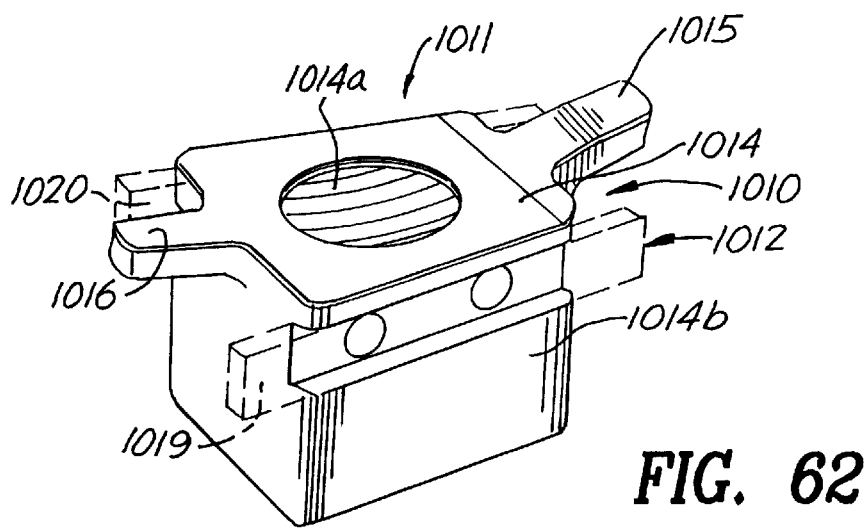
FIG. 62 is an enlarged perspective view of another embodiment of a multi-section infrastructure for forming a dental prosthesis in accordance with the present invention showing a further modified form of the shaped and sized main support bar.
Figure 63:
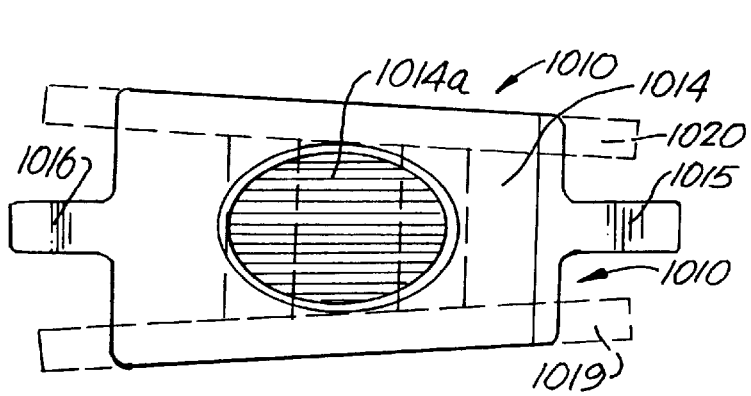
FIG. 63 is a top plan view of the embodiment shown in FIG. 62.
Figure 64:
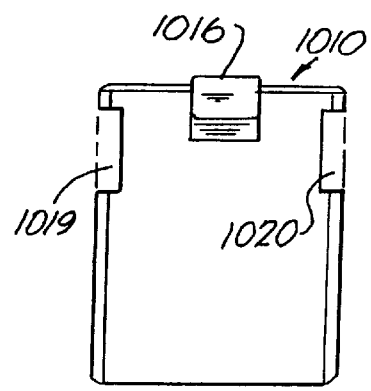
FIG. 64 is a front end view of the multi-section infrastructure for a dental prosthesis as shown in FIGS. 62 and 63.
Figure 65:
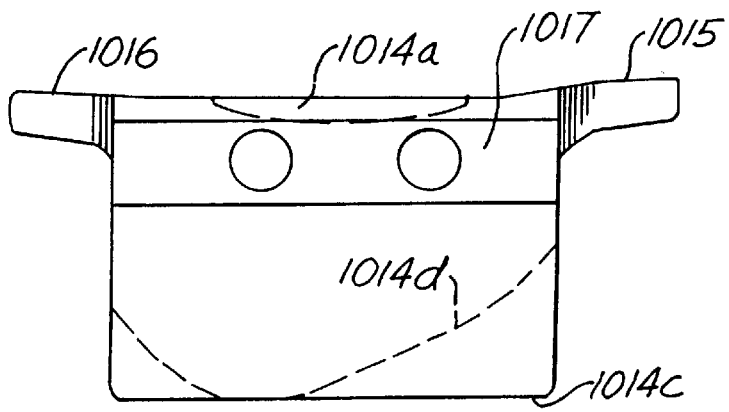
FIG. 65 is a side view of just the main support bar with the side buttress removed.
Figure 66:
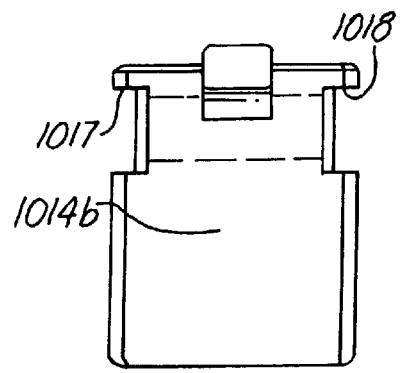
FIG. 66 is a front end view of the main support bar shown in FIG. 65.

While FIGS. 57, 58, 59, 60 and 61 show that the enlarged center section of the main support bar 711 is cut or formed like the embodiments of the invention shown at FIGS. 1 to 8, 18 to 25, 32 to 42 and 49 to 56 of the drawings, to provide longitudinally extending buccal groove 917 and longitudinally extending lingual grooves 918, this embodiment differs from these earlier embodiments in that the vertical space between the inferior and superior borders of these respective grooves 917 and 918 are greater than that of the relatively smaller vertical height of the respective buccal buttress 919 which is mounted in the buccal groove 917 and the lingual buttress which is mounted in the lingual groove 918 to allow for adjustability of these respective buttresses both vertically at each end and for angular positioning relative to the longitudinal line of the multi-section infrastructure 710 when in assembled position as illustrated by the solid and dotted lines for the buccal buttress 919 in FIG. 61.

Such adjustability is obtained because the connecting pins 920a and 920b on the buccal buttress 917 are disposed in assembled position to extend through enlarged transverse bores 921a and 922b, all of which is shown in FIGS. 57, 59, 60 and 61 of the drawings.

These elements are used to coact with the U-shaped pontic clip 913 to provide secondary support depending on the size of the edentulous space and the size and/or number of pontics required to replace the teeth missing in the edentulous space in the patient's mouth.

In the present embodiment the vertically disposed buccal groove 921 and vertically disposed lingual groove 922 and the respective legs 931 and 932 of the U-shaped clip 913 which are fitted into and coact with the transverse grooves 921a and 922a, not shown, are modified in the same manner above described so as to establish predetermined frictional engagement which will enable the main support bar to be adjusted vertically when the U-shaped pontic clip is in assembled position in the buccal and lingual grooves 921 and 922 and to be held in such assembled position until the U-shaped pontic clip 913 is bonded to the main support bar 911 by any suitable cementing means such as a cryogenic or a composite cement.

Thus the multi-section infrastructure in accordance with this embodiment safely holds the U-shaped pontic clip 913 until the main support bar 911 is moved to the optimum adjusted position, at which time the U-shaped pontic clip can be bonded to the main support bar by any suitable means.

STILL ADDITIONAL EMBODIMENTS OF THE INVENTION

Figure 67:
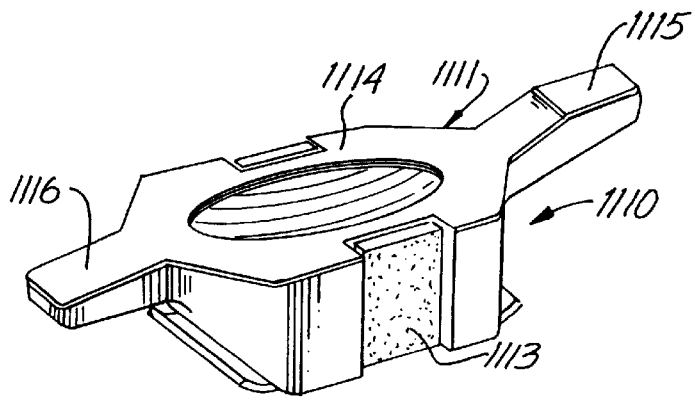
FIG. 67 is an enlarged perspective view of another embodiment of a multi-section infrastructure for forming a dental prosthesis in accordance with the present invention showing a still further modified form of the main support bar and the anterior and posterior connecting ends.
Figure 68:
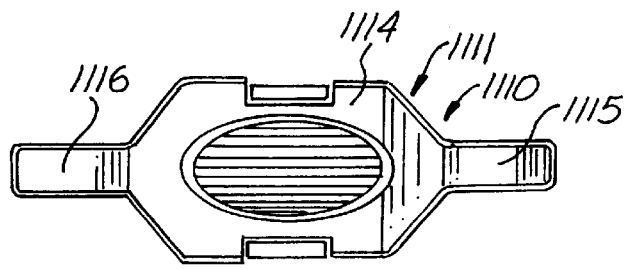
FIG. 68 is a top plan view of the multi-section infrastructure for a dental prosthesis in accordance with the present invention shown in FIG. 67.
Figure 69:
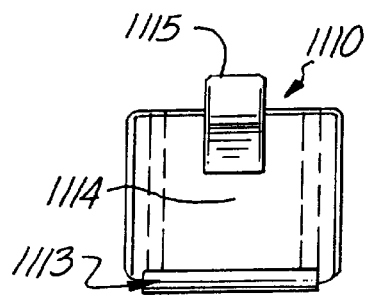
FIG. 69 is a front end view of the multi-section infrastructure for a dental prosthesis as shown in FIGS. 67 and 68.
Figure 71:
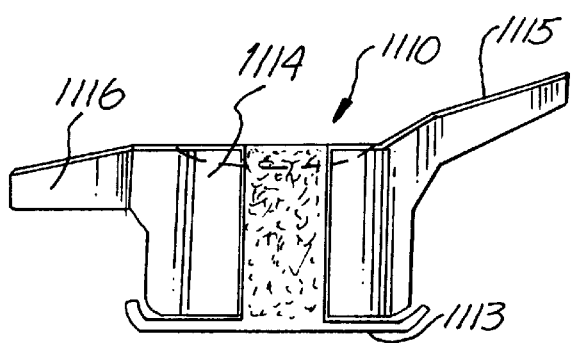
FIG. 71 is a side elevational view of the multi-section infrastructure for a dental prosthesis in accordance with the present invention shown in FIGS. 67, 68, 69 and 70.
Figure 70:
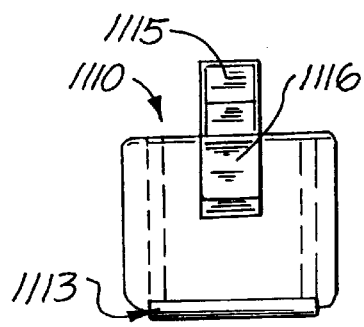
FIG. 70 is a back end view of the multi-section infrastructure for a dental prosthesis as shown in FIGS. 67, 68 and 69.

In the embodiments of the invention shown in the multi-section infrastructure at 1010 of FIGS. 62 to 66 and at 1110 of FIGS. 67 to 69 for forming a dental prosthesis in accordance with the present invention are shaped and sized to meet special requirements for certain edentulous spaces in which a pontic or pontics need to be replaced.

Thus, in FIGS. 62 to 66, the multi-section infrastructure 1010 provides an assembly where the depth of the edentulous space relative the occlusal surface of the tooth or teeth adjacent to the edentulous space is greater than at least 3.5 mm, or further that the curvature of the gingiva in the edentulous space does not conform to the three or four average curvatures for the generally normal edentulous space in a patient's mouth.

In this illustrated embodiment this condition is met by extending the depth of the center section of the multi-section infrastructure and spacing the supplemental or secondary supporting assembly connected to the center section near the upper section thereof.

Thus, referring to FIGS. 62 to 66, the multi-section infrastructure 1010 is shown with a main support bar or beam 1011 and a supplemental or secondary support assembly generally designated 1012. No pontic clip is illustrated for this form of the invention for reasons that will be clear form the comment below regarding meeting the requirements for the curvature of the gingiva for the edentulous space in which the dental prosthesis formed from this type of multi-section infrastructure is used to replace a pontic or pontics.

The main support bar or beam 1011 is a shaped and sized member fabricated as in the earlier form of the multi-section infrastructure above described from any suitable metallic material such as stainless steel alloy, titanium allow, gold alloy, platinum alloy or any FDA approved material to lend the necessary strength to the multi-section infrastructure for the dental prosthesis in accordance with the present invention. The above metallic materials are not by way of limitation because the multi-section infrastructure may also be made from any ceramic, composite or plastic material having sufficient strength and durability for this purpose.

Similar to the earlier form of the present invention described at FIGS. 1 to 8 of the drawings, main support bar or beam 1011 includes an enlarged sized and shaped center section 1014, an anterior connecting end 1015 connected to and continuous with the anterior end of the center section 1015 and a posterior connecting end 1016 also connected to and continuous with the posterior end of the center section 1015. It will be understood that while the anterior connecting end 1015 and posterior connecting end 1016 are shown in general alignment with each other and with the longitudinal line of the main support bar 1011 that the anterior connecting end 1015 and posterior connecting end 1016 may be varied both as to their respective planes and with respect to their curvatures from the longitudinal line of the main support bar 1011 consistent with these various different alignments as above described.

The enlarged shaped and sized center section 1014 also has a hollow concave or indented depression 1014a for the same purposes and objects as above described. The center section 1014 further has a deep or extended lower section 1014b which provides the necessary shape and size to meet the requirements for the correspondingly deep edentulous space in which a pontic or pontics are being replaced and to provide a lower surface 1014c which can be carved, shaped and polished by the Dentist, as illustrated by the dotted line at 1014d, to custom fit the dental prosthesis ultimately formed with this embodiment of the multi-section infrastructure to meet the requirements of the non-uniform gingiva for this or any other type of edentulous space in which a pontic or pontics are being replaced.

The supplemental or secondary supporting assembly 1012 includes a buccal groove 1017 and a lingual groove 1018 which are disposed closer to the upper end of the center section 1014. Mounted in the buccal groove 1017 is a buccal buttress 1019 and in the lingual groove 1018 a lingual buttress 1020.

Other than the fact that this supplemental or secondary supporting assembly 1012 is disposed closer to the upper end of the center section 1014, it is otherwise generally identical to the supplemental or secondary supporting assembly as above described and accordingly no further explanation is deemed necessary for these elements of this embodiment of the multi-section infrastructure 1010.

How the lower face 1014c is curved and shaped by the Dentist will be better understood in the description below on the method for forming and fitting the dental prosthesis in the patient's mouth as more fully set forth below.

In the embodiment of the invention shown at FIGS. 67 to 71 of the drawings, the multi-section infrastructure generally designated 1110 for forming a dental prosthesis in accordance with the present invention is shaped and sized to meet the requirements of a relatively deep edentulous space where the occlusal surfaces of the teeth on the anterior side and posterior side of the edentulous space are on sharply different planes.

In this situation the molars tend to lean into the empty edentulous space. Thus, the supporting tooth on the anterior side of the edentulous space will have an occlusal surface that is substantially higher than the occlusal surface for the supporting tooth on the posterior side of the edentulous space.

In this form of the multi-section infrastructure, the anterior connecting end and the posterior connecting end can be custom fitted to meet the problems which this presents in the formation of a dental prosthesis in accordance with the present invention.

Thus referring to FIGS. 67 to 69, multi-section infrastructure 1110 has a main supporting bar or beam 111 operatively associated with a pontic clip 1113.

Main supporting bar 1111, as in the case of the earlier form above described, will be made of a metal alloy or other suitable material which is FDA approved.

Further, main supporting bar 1111 will have a center section 1114, an anterior connecting end 1115 connected to and continuous with the anterior end of the center section 1114 and a posterior connecting end 1116 connected to and continuous with the posterior connecting end of center section 1014. Anterior connecting end 1115 is in a different place than that of the posterior connecting end 1116 to illustrate multi-section infrastructure 1110 adapted for use in an edentulous space where the planes of the occlusal surfaces of the respective anterior support tooth differs from that of the posterior support tooth.

As will be clear from FIGS. 67, 69, 70 and 71 of the drawings that the anterior connecting end 1015 and posterior connecting end 1016 are on different planes and therefore they can meet the problem which occurs when the occlusal surface of the supporting tooth at the anterior end of the edentulous space in which a pontic or pontics are being replaced differs sharply from the occlusal surface of the supporting tooth at the posterior end of such edentulous space.

Further, however, while the anterior connecting end 1115 and the posterior end 1116 are shown as having a given length and are in alignment with each other, the Dentist can custom fit the main support bar or beam 1111 into assembled position so as to position the center section 1114 of the main support bar or beam 1111 properly in the edentulous space by using a dentist orthodontic pliers and grinding means to cut and bend the anterior connecting end 115 and/or the posterior connecting end 1116 to a desired length or to bend these elements to fit in the occlusal preparation in the teeth adjacent to the edentulous space.

The pontic clip 1113 may be any one of the pontic clips as above described and shown in the drawings and is used for the same object and purposes as has been above described.

METHOD AND PROCESS FOR FORMING THE DENTAL PROSTHESIS

These embodiments for the improved multi-section infrastructure as above described are respectively alternatively selectable for establishing the dental prosthesis in accordance with the present invention having, a pontic or pontics for filling the edentulous space adjacent to and between the patient's teeth. This can be done by two methods which are also selectable in the alternative by the Dentist fabricating the dental prosthesis. First, by direct "in situ" procedures in the patient's mouth, or second, by an indirect procedure, exterior of the patient's mouth, using a stone cast model of the edentulous space and its adjacent tooth or teeth.

A. "IN SITU" Formation of a Dental Prosthesis

Figure 72:
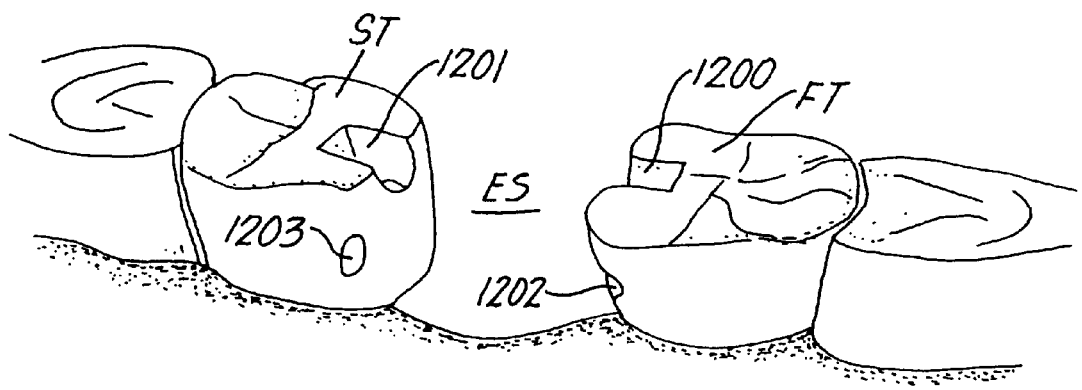
FIG. 72 is an enlarged perspective view of a portion of the posterior teeth in a patient's mouth showing an edentulous space with a first tooth disposed adjacent the anterior end of the edentulous space and a second tooth disposed adjacent the posterior end of the edentulous space and wherein the respective first tooth and second tooth have been prepared to provide the occlusal mounting grooves for the oppositely disposed and spaced anterior and posterior connecting ends on the main support means for the dental prosthesis and side indentations for the ends of the buccal and lingual buttresses of the embodiment of the multi-section infrastructure or assembly for a dental prosthesis as shown in FIGS. 1 to 8 of the drawings.
Figure 73:
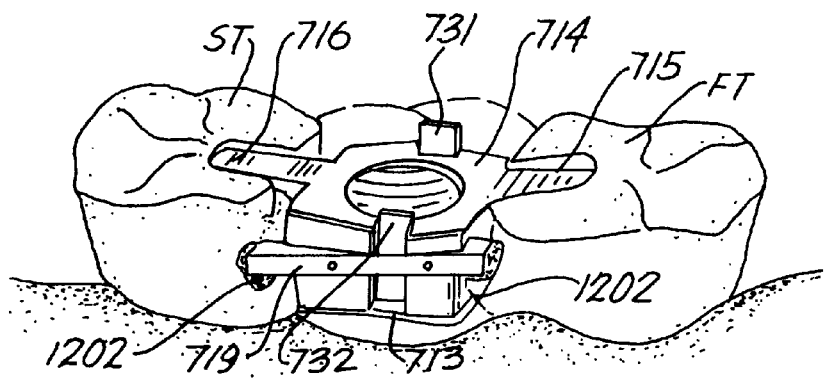
FIG. 73 is an enlarged top perspective view of the edentulous space in the posterior teeth as shown in FIG. 72 with the elements of the multi-section infrastructure or assembly for a dental prosthesis as shown in FIGS. 18 to 25 or FIGS. 57 to 62 of the drawings assembled and positioned in the edentulous space with the connecting ends for the main support bar extending into the occlusal mounting grooves and the buccal and lingual side buttresses extending into the side indentations in the first tooth and second tooth at the respective anterior and posterior ends of the edentulous space.
Figure 74:
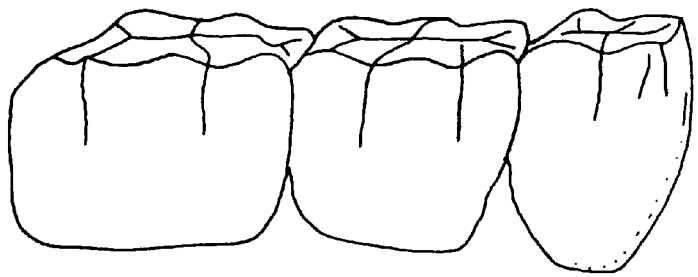
FIG. 74 is an enlarged perspective view of the formed dental prosthesis in accordance with the present invention with a single pontic thereon fixed into assembled position in the patient's teeth disposed on opposite sides and adjacent to the edentulous space.
Figure 75:
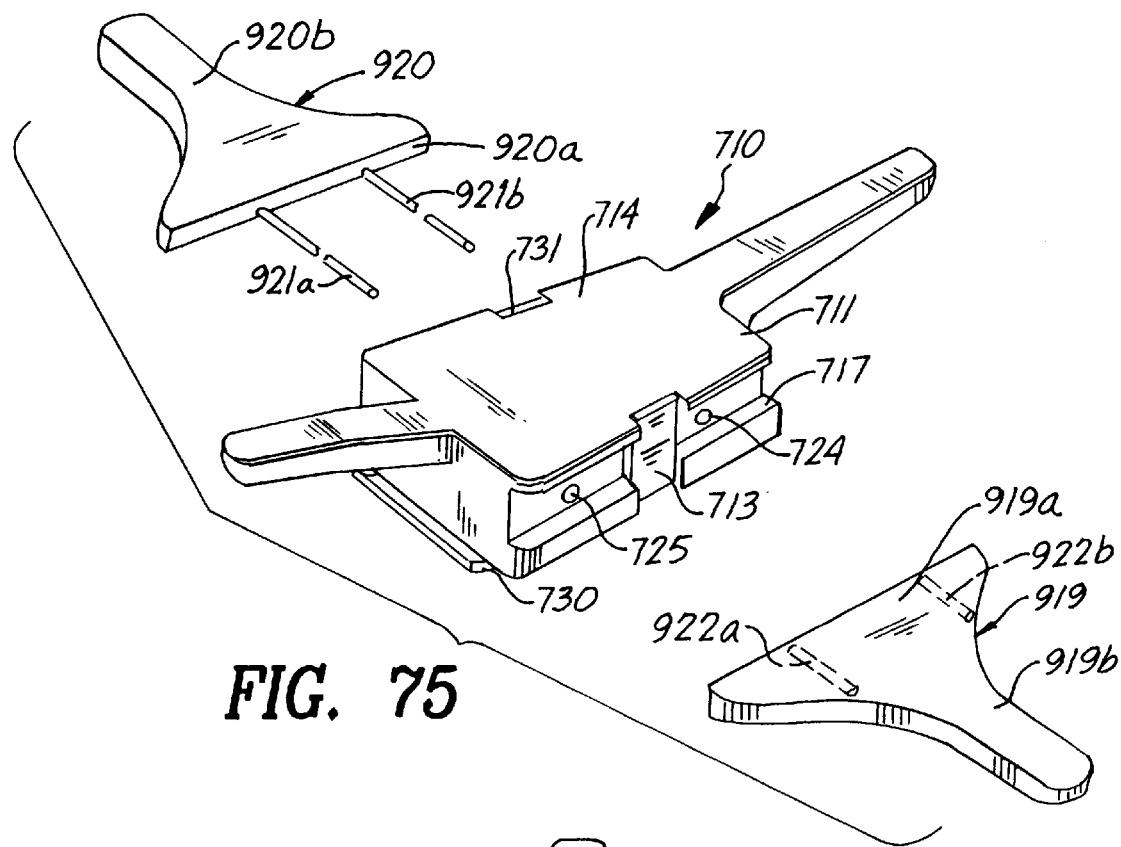
FIG. 75 is an enlarged perspective and exploded view of the main support bar or beam for the multi-section infrastructure shown in FIGS. 32 to 48 of the drawings disposed for operative association with a buccal side shim and lingual side shim, used in the indirect method of pontic creations in accordance with the present invention.
Figure 76:
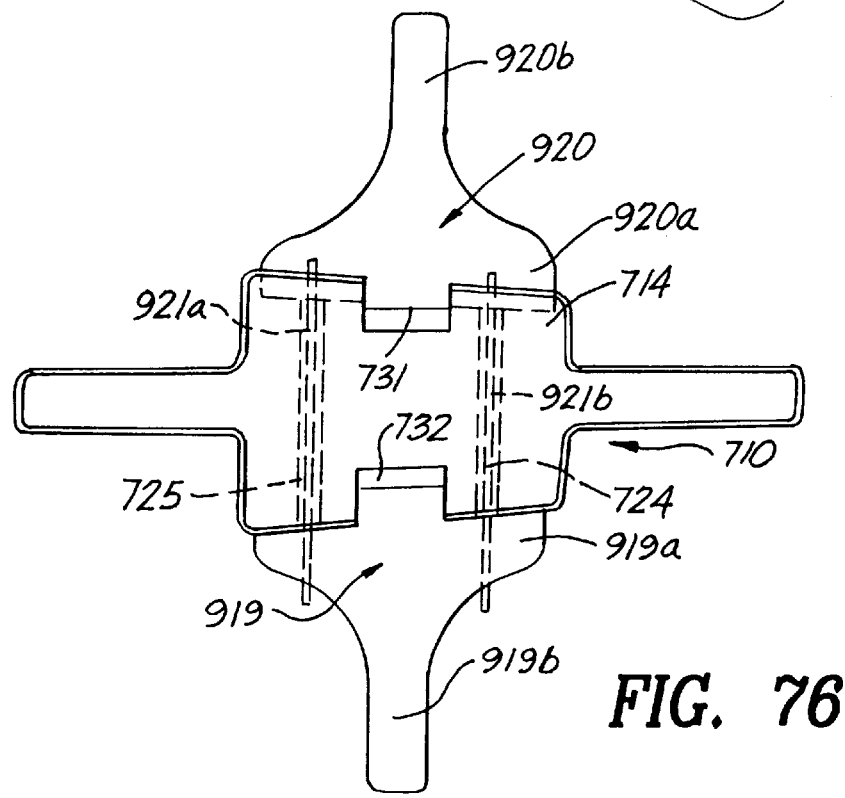
FIG. 76 is a top plan view of the main support bar or beam for the multi-section infrastructure shown in FIGS. 32 to 48 with the buccal side shim and lingual side shim in assembled position.
Figure 77:
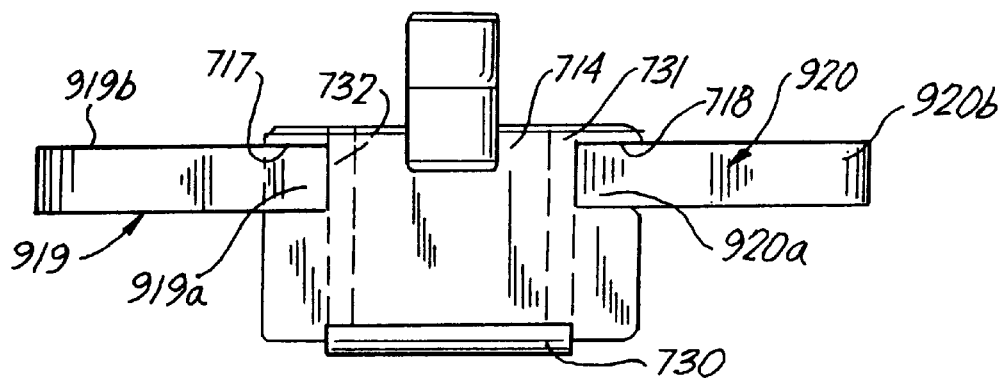
FIG. 77 is a front view of the main support bar or beam for the multi-section infrastructure shown in FIGS. 32 to 48 with the buccal side shim and lingual side shim in assembled position.

The steps of this method are best understood by reference to FIGS. 72, 73 and 74 of the drawings which show the fabrication of a dental prosthesis with a single pontic for replacement of a missing tooth in an edentulous space ES in a patient's mouth between a first tooth FT anterior of the edentulous space and a second tooth ST posterior of the edentulous space.

The patient's bite is first adjusted by normal equilibration techniques. Potential or actual infection of the gums and any cavities in the teeth are all corrected before the further procedures are followed.

In the periodontal ligament space of each of the first and second teeth adjacent to the edentulous space, the patient's gums are first anesthetized by infiltration and/or intraligamentary anesthesia. Then using a 558 fissure or similar burr, inserts or grooves are cut as at 1200 in the occlusal surface of the first tooth FT and similarly as at 1201 in the occlusal surface of the second tooth ST adjacent to the anterior and posterior ends of the edentulous space ES. The depth of the occlusal inserts or grooves 1200 and 1201 should be at least 3.00 mm deep into the occlusal-proximal of the respective anterior and posterior teeth FT and ST and will be in minimum outline form for a class 1 cavity preparation but will go through the marginal ridge of the respective teeth in the portion adjacent to the edentulous space ES. For longer edentulous spaces where buccal and/or lingual buttresses are required, bilateral indentations as at 1202 on the anterior tooth FT and at 1203 in the posterior tooth ST are cut during the fitting of the dental prosthesis in assembled position in the edentulous space as described below.

When there is adequate occlusal to gingival height on a given tooth adjacent to the edentulous space, a diamond burr or an appropriate carbide burr, such as a Brasseler 1158 TC burr, can be used for cutting the proximal wall to create parallel walls with excellent undercuts. The side walls of the inserts or grooves 1200 and 1201 follow the perimeter outlines.

After the teeth are thus prepared, the following steps illustrate how one embodiment, for example, the infrastructure shown in FIGS. 32 to 42 of the drawings, can be fitted into assembled position by this "in situ" method.

1.1 Acid etch the respective anterior tooth FT and posterior tooth ST, twenty to thirty seconds for the enamel and five to ten seconds for the dentine. Then wash and dry these respective teeth.

1.2 Apply to each of the respective anterior and posterior teeth FT and ST at least five coats of any suitable primer such as "Allbond-Primer A,B,", a product available in the commercial marketplace, and then place a bonding resin on the respective teeth and cure the resin. One may also use a ,one step, primer-resin combination for this step which is also available in the commercial marketplace.

1.3 Occlusal grooves or grooves as at 1200 and 1201 are cut in the respective tooth or teeth as above described.

1.4 The main support bar or section 711 which has the desired average length to fill the edentulous space ES is selected and is now adjusted and fitted by removing a portion of the anterior connecting end 715 and the posterior connecting end 716 by grinding or cutting the length of the respective anterior connecting end 715 and posterior connecting end 716 so that the shaped and sized center section 714 for the multi-section infrastructure 710, or such main supporting bar or section from any of the other multi-section infrastructures as described herein, is generally centered in the edentulous space ES, and the sized anterior connecting end 715 and posterior connecting end 716 rest respectively in the occlusal grooves 1200 and 1201.

1.5 If a pontic clip is to be used, after establishing the fit of the main support bar or beam 711, the main support bar 811 is removed and a pontic clip having, a center section matching the length and the curvature of the edentulous space ES is selected and placed on the main support bar or beam 711. The main support bar 711 with the pontic clip attached is replaced in position in the edentulous space and while the anterior connecting end 715 and posterior connecting end 716 rest in the respective associated occlusal grooves 1200 and 1201, the selected pontic clip is pushed towards the gingival occlusal surface in the edentulous space until the base section rests lightly on the gingival surface. By reason of the frictional engagement of the pontic clip with the grooved surfaces of the vertical buccal groove and the vertical lingual groove, the selected pontic clip will remain in this pre-assembled position and thereafter will be permanently cemented to the main support bar in this assembled position. The side legs which are above the occlusal surface of the main support bar are removed as by grinding the extra length off with a suitable dental burr.

1.6 The main support bar with the pontic clip attached is now removed, and after acid etching all cut surfaces of the respective supporting tooth or teeth, the dual cure bonding cement or suitable bonding resin is placed in the occlusal grooves 1200 and 1201, and the main support section or beam 711 is now returned to assembled position, with the pontic clip selected thereon, so that the anterior connecting end 715 and posterior connecting end 716 rest in the partially filled occlusal grooves 1200 and 1201 in the respective anterior tooth FT and posterior tooth ST.

1.7 With the main support bar or beam 711 fitted in this generally assembled position, it can be used as a guide for placing the indentations 1202 and 1203 at the line angles on the respective proximal walls of the anterior tooth FT and the posterior tooth ST by running a fissure or similar dental burr along the superior surface of the respective buccal groove and lingual groove in the main support bar and then along the inferior surface of the same respective buccal and lingual groove, directly into the proximal surface of the anterior tooth FT and the posterior tooth ST adjacent to the edentulous space, for a depth of approximately 1.5 mm.

1.8 Thus, the spaced indentations or dimples are cut at sites which are linear extensions of the anterior and posterior ends of the respective buccal groove and lingual groove as illustrated at 1202 on the buccal side of the mesial proximal wall of the anterior tooth FT and 1203 on the buccal side of the distal proximal wall of the posterior tooth ST as is shown in FIGS. 72 and 73 of the drawings. Similar indentations, not shown, are prepared or cut in the lingual side of the mesial proximal wall of the anterior tooth FT and the lingual side of the distal proximal wall of the posterior tooth ST.

1.9 The lingual buttress with the transverse connecting pin or pins attached is next mounted into the lingual groove in the central section for the main support bar of the multi-section infrastructure for forming the dental prosthesis by passing the pin or pins through the associated transverse bore or bores and pulling the lingual tightly against the lingual groove by holding the pins with the thumb and index finger. The lingual buttress is now bonded into position. The connecting pins which are used to so hold the lingual buttress securely until bonded into assembled position also serve the purpose of providing for subsequent fitting and engagement with the aligned holes in the buccal buttress thus now permitting the buccal buttress to be tightly mounted and correctly oriented in the buccal groove. With this assembly procedure, the respective lingual buttress rests snugly against the lingual side of the adjacent anterior and posterior supporting tooth or teeth, and the buccal buttress rests tightly against the buccal side of these respective anterior and posterior supporting tooth or teeth.

1.10 The lingual buttress is now sized at its ends so that it fits into the respective anterior lingual indentation in the proximal of the anterior supporting tooth FT and the posterior lingual indentation in the proximal of the posterior supporting tooth ST. By using suitable self-curing bonding, the lingual buttress is now cemented and fixed in assembled position with the transverse connecting pin or pins extending through the transverse bore or bores for communication with the buccal buttress. These steps of cementing the lingual buttress into position first is to facilitate the subsequent placement of the buccal buttress. Once the lingual buttress is affixed in assembled position, it is then easier to affix the buccal buttress into assembled position because the connecting pin or pins are now in a fixed position and cannot move as the buccal buttress is mounted on the pins and also fixed in assembled position.

1.11 Thus after the lingual buttress is affixed in assembled position, the buccal buttress is sized at its ends so that it fits into the respective anterior buccal indentations in the proximal of the anterior supporting tooth FT and the posterior buccal indentation in the proximal of the posterior supporting tooth ST. By applying suitable bonding resins and curing the resins, the buccal buttress can be fixed in assembled position. Last, the extending ends of the connecting pin or pins are then cut or ground off flush with the outer face of the buccal buttress and all the parts are treated with dual cure bonding cement or resin and the entire assembly cured to connect the parts and cement them into assembled position to provide the multi-section infrastructure 710, as illustrated, for the dental prosthesis.

1.12 The pontic can now be built-up about the multi-section infrastructure with bonding material and cured until large enough either to receive a tooth mold partly loaded with composite material, or to permit the Dentist to free hand fashion the bonding material until the desired shape for the given pontic or pontics are obtained.

1.13 If the pontic is fabricated with a tooth mold on the preformed multi-section infrastructure of the dental prosthesis, a celluloid mylar, polyethylene or similar clear plastic crown form is cut and formed with a slot or opening at the respective mesial and distal proximal ends so that the crown form will fit over the preformed base of composite material and about the oppositely projecting connecting ends of the main support bar or beam 711.

1.14 The crown form is positioned on the preformed base of composite material, and the gingival edges are trimmed. The occlusal surface of the crown form is designed to be approximately 1.25 mm below the plane of the occlusal surface of the teeth FT and ST adjacent to the edentulous space in which the tooth or teeth are being replaced.

1.15 The crown form is now removed, filled with composite material and then pushed and pressed onto the preformed base of composite material about the shaped and sized wide center section 12 on the main support bar or beam 11 until the gingival edges of the crown form are firmly seated against the surfaces corresponding to the gingiva or gum line of the edentulous space in the patient's mouth.

1.16 When in this position, the composite material is subjected to ultra-violet light to cure and harden the pontic or pontics into their initial rough form.

1.17 Thus, with the above steps a dental prosthesis with a roughly formed pontic or pontics replacement unit thereon is provided having an approximate custom fit for the edentulous space in the patient's mouth in which the tooth or teeth have to be replaced.

1.18 The mold form can then be removed and the formed pontic or pontics sculpted and trimmed to provide the desired finished shape.

1.19 During the build-up of the given pontic or pontics, embrasures are kept open by using a perio-probe or similar instrument horizontally, and then a wedge-like instrument to provide the exact shape to meet hygienic needs.

1.20 The occlusal surface or surfaces on the pontics for a given dental prosthesis are approximately 1.25 mm lower than the occlusal surfaces of the supporting tooth or teeth adjacent to the edentulous space. This surface or surfaces is now covered with soft composite on top of which is placed a clear thin transparent material such as "SARAN WRAP™" or polyethylene. The patient is then told to bite to a completely closed position and then open. The occlusal shaped surface formed on the composite covered pontic or pontics of the dental prosthesis by the indentations from contact with the opposite tooth or teeth is then cured, and effectively the occlusion between the upper teeth and the lower teeth in the patient's mouth can be adjusted in just minutes.

1.21 After the occlusal surfaces of the composite material from which the pontic is formed are completely sculpted and polished, the composite material is again acid etched, washed, dried and a partly filled hydrophilic resin such as the resin sold in the commercial marketplace under the trademark "FORTIFY" is used to resurface the composite, to resecure any loose filler. "FORTIFY", a Bisco Product readily available in the commercial marketplace, is a partly filled resin with components which act to slow down wear of the composite material. This or a similar material is used as a final outer coating to reseal the outer surfaces of the composite that have been ground or carved during the formation of the pontic in the dental prosthesis in accordance with the present invention and the method of 'in situ' fabrication of such dental prosthesis as above described. The final product showing the replacement of a single pontic in the edentulous space ES of FIG. 72 is as shown in FIG. 74.

B. Exterior Formation of Dental Prosthesis on a Cast Model

Cast model when used herein refers to any of the well known dental techniques for forming models of a patient's teeth and gums from materials also well known which harden into devices generally referred to as stone cast models. Since these devices and methods are well known to those skilled in the art, they will not be more fully described.

The forming or fabrication of a dental prosthesis in accordance with the present invention on a stone cast model exterior of the patient's mouth provides the Dentist with additional freedoms and options over the preparation of such dental prosthesis by the "in situ" procedure as above described. When the Dentist fabricates a dental prosthesis from any of the multi-section infrastructures as above described, the Dentist can save valuable time by assigning the fabrication of such dental prosthesis to an associate or a laboratory technician exterior of the patient's mouth on such stone cast model of the edentulous space where the tooth or teeth are being replaced and the supporting tooth or teeth adjacent thereto.

Formation of the dental prosthesis on the stone cast model differs from the "in situ" procedure, as above described, in that after the dental prosthesis is formed, it must be transferred from the stone cast model and be assembled, fitted and affixed to the supporting tooth or teeth adjacent to the edentulous space in the patient's mouth and then appropriately finished in such assembled position.

To achieve this end, the method of fabricating the dental prosthesis on a stone cast model utilizes "shims" or "spacers" in the multi-section infrastructure for the given dental prosthesis which occupy the buccal and lingual grooves in the enlarged center section of the main support section or bar of the multi-section infrastructure selected while the dental prosthesis is being formed in the stone cast model. The purpose of the shims is to occupy the respective buccal groove and lingual groove during fabrication of the tooth or teeth on the given multi-section infrastructure, so as to maintain these respective grooves totally open and clear along the entire respective groove length and within the transverse bores. This enables the Dentist in the final formation of the dental prosthesis to place the respective buccal buttress and lingual buttress in these respective buccal grooves and lingual grooves without interference in the preparation of further steps for fixing the dental prosthesis permanently in assembled position in the patient's mouth.

These "shims" or "spacers" are used to prevent the buccal groove, the lingual groove and the transverse connecting pin bore or bores from being filled with the cement, composite or hard toothlike materials that are used to build up the pontic or pontics during the formation and preparation of the preliminary dental prosthesis with the replacement pontic or pontics thereon before it is moved from the stone cast model into the patient's mouth where it is assembled, fixed and finished to position the replacement pontic or pontics in the associated edentulous space.

The actual buccal and lingual buttresses for the given dental prosthesis being formed on the stone cast model of the edentulous space and the associated tooth or teeth cannot be used on the stone cast model because they would be locked in by the cement or composite during the formulation of the pontic or pontics for the given dental prosthesis and effectively the given dental prosthesis thus formed could not be removed from the stone cast model.

Thus, when the Dentist, dental assistant or lab technician is preparing the preliminarily formed dental prosthesis which is removed from the stone cast model to fit it into assembled position in the edentulous space in the patient's mouth these "shims" or "spacers" prevent cement or composite from filling the buccal and lingual grooves and transverse connecting pin holes as the pontic or pontics are being created so that when the "shims" or "spacers" are removed, the secondary supporting assembly defined by the buccal and lingual buttresses can be positioned in the main support bar or beam and attached into assembled position in the supporting tooth or teeth in the patient's mouth in the same manner as was above described for the "in situ" formation of the dental prosthesis. This will be better understood by reference to the description which follows.

Thus, for forming a dental prosthesis, for example, like the embodiment of the present invention shown at FIGS. 32 to 42 of the drawings, reference to which is shown by the same character numerals and is only by way of illustration and not limitations, FIGS. 75, 76, 77, 78, 79, 80 and 81 show that the main support bar or beam 711 for this form of the multi-section infrastructure 710 in accordance with the invention has operatively associated with the respective buccal groove 717 and lingual groove 718 a buccal shim 919 and a lingual shim 920 sized to fit into the respective buccal groove 717 and lingual groove 718.

Lingual shim 920 is shaped and sized to form a running fit with the lingual groove 718 so that elongated orienting pins as at 921a and 921b projecting generally normal from an inner edge 920a on the lingual shim 920 will during assembly of the lingual shim 920 into the lingual groove 718 slide into and through the transverse connecting pin bores 724 and 725 in the enlarged shaped center section 714 of the main support bar 711 of this multi-section infrastructure 710 for the dental prosthesis in accordance with this form of the present invention and extend or project a substantial distance beyond the buccal side of the enlarged shaped center section 714 to receive the buccal shim thereon.

At the outer edge or side of the lingual shim 920, a shaped gripping or handling tab 920b is provided which projects laterally in a direction opposite from the orienting pins 921a and 921b. This laterally projecting gripping or handling tab is so sized that it can be easily grasped and used for both setting the lingual shim 920 into assembled position in the lingual groove 718 and for removing the lingual shim 920 to expose the lingual groove 718 preparatory to moving the partially formed dental prosthesis from the stone cast model to the edentulous space in the patient's mouth.

Similarly, buccal shim 919 has an inner edge 919a and a grasping or handling tab 919b with matching bores as at 922a and 922b, also extending normal to the inner edge 9190a for the buccal shim, so the buccal shim can be grasped to fit the inner edge 920a into the buccal groove 717 and onto the projecting ends of the elongated orienting pins 921a and 921b, all of which is clearly shown in FIGS. 75, 76, 77 and 81 of the drawings.

When the enlarged shaped center section 714 is fitted with the lingual shim 920 and buccal shim 919 as above described, the preliminary forming of the dental prosthesis can now proceed on the stone cast model exterior of the patient's mouth.

Prior to utilizing this technique for forming the dental prosthesis on a stone cast model exterior of the patient's mouth, all the same preliminary steps of preparing the supporting tooth or teeth adjacent the edentulous space in the patient's mouth as above described for the "in situ" formation of the dental prosthesis are first followed. Then the following steps are continued:

2.1 After the occlusal grooves have been prepared in the anterior and posterior teeth adjacent to the edentulous space, in which the pontic or pontics needs to be replaced, an impression is taken of the edentulous space and the adjacent supporting tooth or teeth with a rapid set polysiloxane or similar material.

Figure 78:
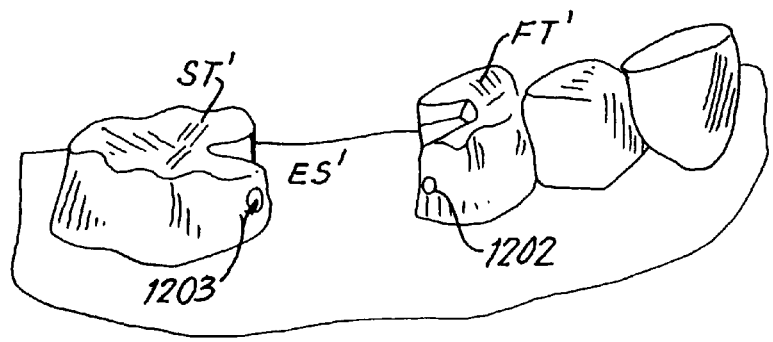
FIG. 78 is an enlarged perspective view similar to FIG. 72 showing, however, a stone cast model of the portion of the posterior teeth in a patient's mouth having an edentulous space with a first tooth disposed adjacent the anterior end of the edentulous space and second tooth disposed adjacent the posterior end of the edentulous space wherein the respective first tooth and second tooth have been prepared to provide the occlusal grooves and mounting proximal grooves for the oppositely disposed and spaced connecting ends and side buttresses of the infrastructure for the dental prosthesis shown in FIGS. 18 to 31 and FIGS. 32 to 48 of the drawings.
Figure 79:
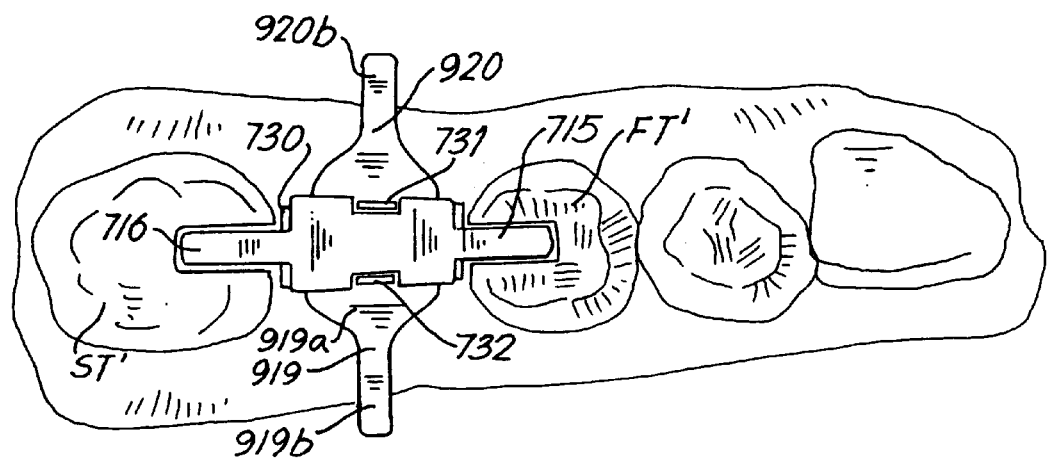
FIG. 79 is a top plan view of the stone cast model of the edentulous space in the patient's mouth as shown in FIG. 78 with the embodiment for a multi-section infrastructure as shown in FIGS. 32 to 48 of the drawings mounted with the connecting ends of the main support bar in assembled position in the preparation in the respective occlusal surfaces of the anterior and posterior teeth adjacent to the edentulous space which is to receive the pontic or pontics replacement and the removable buccal side shim and lingual side shim in position before the dental prosthesis is formed on the cast model.
Figure 80:
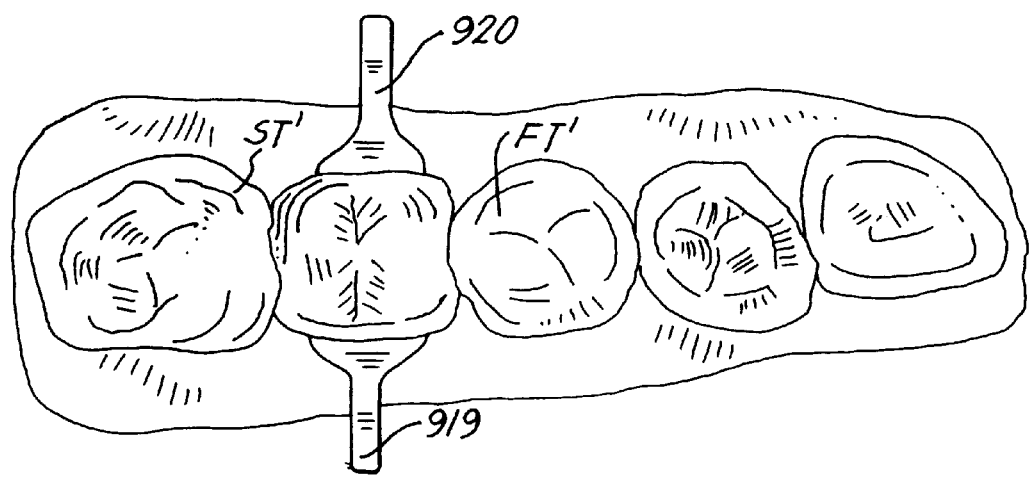
FIG. 80 is the same view as FIG. 79 showing the preliminary formation of the dental prosthesis on the cast model before the dental prosthesis with the buccal and lingual side shims thereon is removed from the stone cast model for placement into the edentulous space in the patient's mouth.
Figure 82:
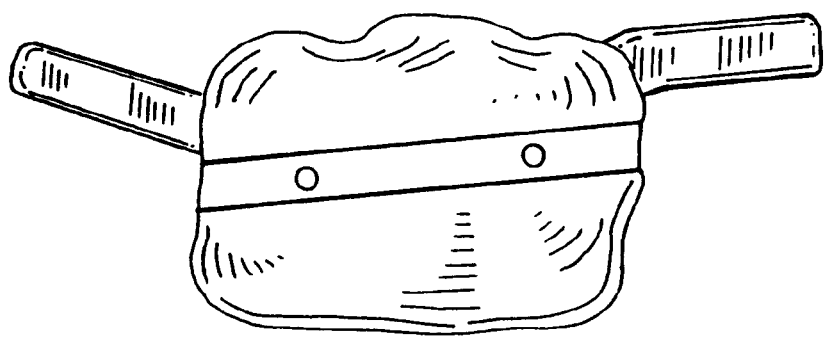
FIG. 82 is a side elevational view of the preliminarily formed dental prosthesis as shown in FIGS. 80 and 81 with the buccal and lingual side shims removed.
Figure 83:
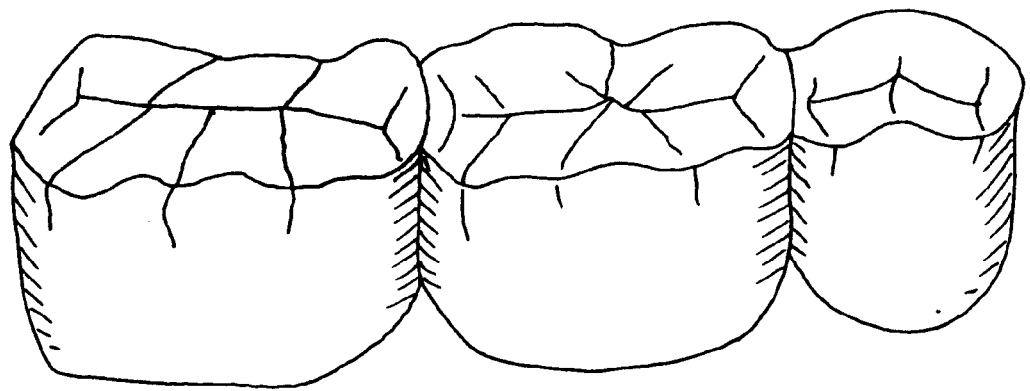
FIG. 83 is a perspective view of the dental prosthesis shown in FIGS. 75 to 82 in assembled position in the patient's mouth.

2.2 This impression is poured up at a point exterior of the patient's mouth by means of a fast set "grey rock" or plaster material to form the stone cast model of the support teeth and the edentulous space in which the tooth or teeth need to be replaced. One stone cast model so formed is shown at FIG. 78. It is similar to the teeth with an edentulous space as shown at FIG. 72 and thus shows edentulous space ES' and the adjacent anterior tooth FT' and posterior tooth ST'. This procedure is well known in the dental profession and therefore is not more fully described.

2.3 This stone cast model is removed to a work station or dental laboratory in the dental office where forming and fabricating of the dental prosthesis occurs. In this illustration, the embodiment of the infrastructure shown at FIGS. 32 to 42 of the drawings will be used again to show how the stone cast model exterior of the patient's mouth is used for fabricating a dental prosthesis in accordance with the present invention.

2.4 Thus, at the work station or laboratory exterior of the patient's mouth, the multi-section infrastructure for this embodiment of the dental prosthesis is preliminarily formulated by positioning and fitting the legs or flanges 731 and 732 of the pontic clip 713 relative the main support bar or beam 711 until the roughened inner surfaces of the side walls 733 and 734 are disposed in sliding engagement with the respective grooved or roughened inner surfaces as at 721*a* and 722*a* of the buccal groove 721 and lingual groove 722 in the wide center section 714 of the main support bar or beam 711.

2.5 The assembled infrastructure is now positioned in the stone cast model by sliding the main support bar or beam 711 generally down relative the pontic clip 713 until the oppositely disposed connecting ends 715 and 716 rest on the floor of the occlusal preparations in the respective spaced anterior tooth FT' and posterior tooth ST' in the stone cast model while base section 730 of the pontic clip 713 touches the equivalent gingival surface in the center portion of the edentulous space ES' between the spaced teeth FT' and ST' on the stone cast model corresponding to the gingival surface of the actual edentulous space in the patient's mouth.

2.6 This positioning and orientation of the multi-section infrastructure 710 for this form of the dental prosthesis is carefully adjusted and checked, and then the main support bar or beam 711 and the pontic clip 713 are bonded and cemented together with cyano-acrylic, dual cure bonding resin or cement and joined at the joint formed between the grooved or roughened buccal surface 721*a* of the buccal vertical groove 721 and grooved or roughened lingual surface 722*a* of lingual vertical groove 722 in the enlarged center section 714 of the main support bar or beam 711 and the grooved or roughened inner walls 733 and 734 of the legs 731 and 732 of the pontic clip 713, all of which is clearly shown by FIGS. 32, 33, 37, 43, 43A, 75, 76, 77 and 79 of the drawings.

2.7 Once these cemented joints have set, the assembled main supporting bar or beam 711 of this form of the multi-section infrastructure 710 can be ground or otherwise adjusted to remove the excess projecting height of the legs or flanges 731 and 732 of the pontic clip 713 until the occlusal surface of the wide center section 714 of the main support bar or beam 711 and the upper ends of the legs 731 and 732 are generally flush with each other.

2.8 In order to preliminarily form the pontic or pontics on this assembly of the main support bar or beam 711 and the pontic clip 713, the two transverse bores 741 and 742, the buccal groove 717 and lingual groove 718 are coated with a suitable thin oil such as mineral oil.

2.9 A lingual "shim" or "spacer" 919 with the spaced projecting orienting rods 921*a* and 921*b* now is tested and its mesial and distal extensions modified as may be necessary to fit through the transverse bores 741 and 742 into the lingual groove 717 in the enlarged center section of the main support bar or beam 711 so that it fits and engages with the buccal shim or spacer 920 and is disposed in snug engagement with the adjacent side of the pontic clip 713. Thus when the lingual shim 919 is positioned, the connecting rods 921*a* and 921*b* will extend through the connecting pin bores 922*a* and 922*b*, see FIGS. 75 and 76, from the lingual to the buccal side of the stone cast model, the inner edge of the lingual shim 919 will rest in the lingual groove so that the inner edge of the lingual "shim" lies external of the adjacent outer face of the pontic clip 713 and the respective opposite mesial-distal ends will lie between the anterior tooth FT' and posterior tooth ST', as is clearly shown in FIG. 79.

2.10 At the buccal side of the stone cast model, the buccal "shim" 920 is provided with spaced and longitudinally extending bores 922*a* and 922*b* into which the projecting connecting rods 921*a* and 921*b* of the lingual "shim" 919 extend. The buccal shim 920 is adjusted mesially and distally and also modified and placed so that in assembled position in the buccal groove in the enlarged center section, it will fit onto the projecting connecting rods 921*a* and 921*b* and over the adjacent outer buccal face of the pontic clip 713 and will be between the anterior tooth FT' and the posterior tooth ST', as is also clearly shown in FIG. 79.

2.11 Composite is now built up on the buccal and lingual sides of the main support bar or beam 711 until the tooth shape has been preliminarily developed above and below the respective lingual "shim" 919 and buccal "shim" 920, going down to the equivalent ridge line on the stone cast model and to the occlusal surface but not on it for the pontic in formation. The composite is then cured.

Figure 81:
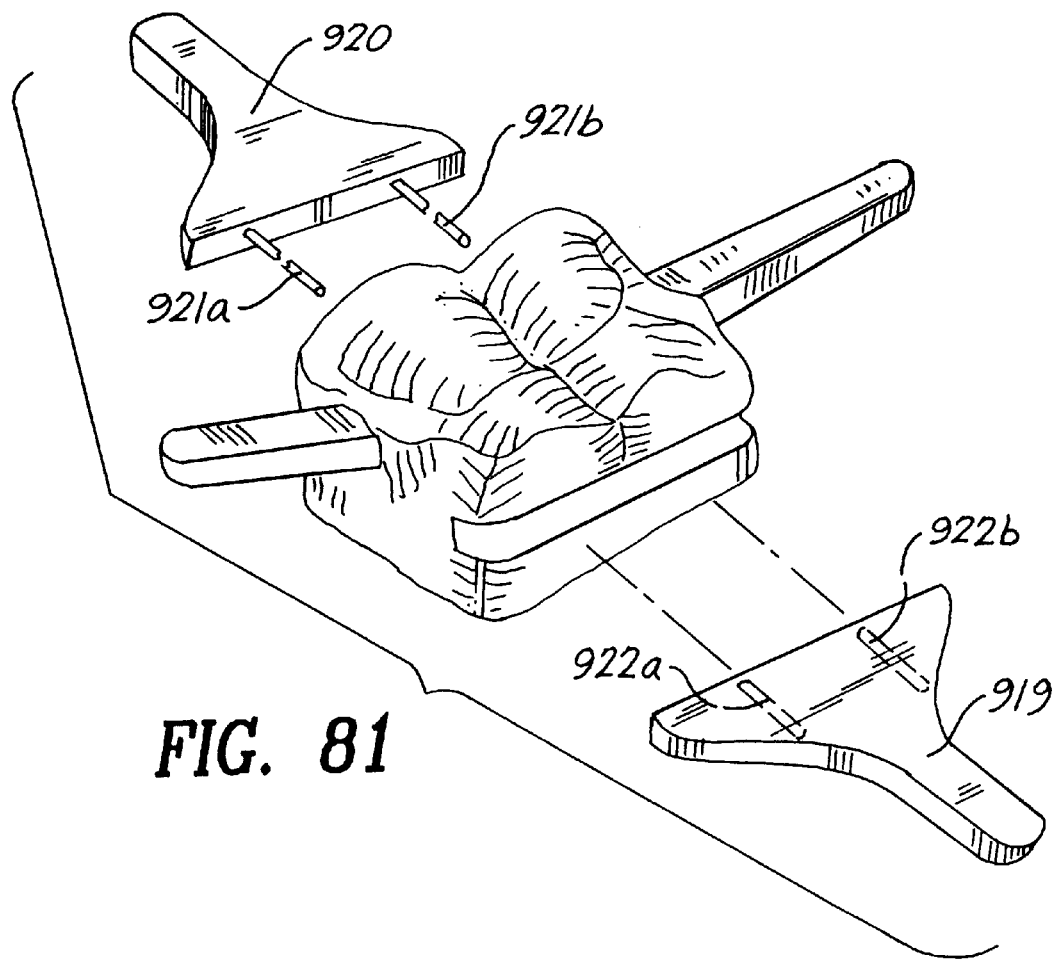
FIG. 81 is an enlarged perspective view of the preliminarily formed dental prosthesis where the respective buccal side shim and lingual side shim have been removed to prepare the dental prosthesis for receiving the buccal and lingual buttresses and for fitting into assembled position in the patient's mouth.

2.12 The buccal and lingual "shims" are now removed by the small handle sections 919*b* and 920*b*, first the lingual "shim" and then the buccal "shim" being removed. If the respective buccal and lingual "shims" are made from a material to which composite will not stick; such as "TEFLON", "DELRIN" or similar synthetic polymers of which there are many purchasable on the open market; they will be removed easily from their assembled position in the dental prosthesis being formed on the stone cast model, as is shown by FIG. 81 of the drawings.

2.13 This preliminarily formed pontic will now be removed from the stone cast model and highly polished before it is returned to the patient's mouth. FIG. 81 shows that this preliminary pontic has the general shape of a tooth with the buccal groove 717 and lingual groove 718 exposed so that the metal of the enlarged center section and the respective buccal exterior face and lingual exterior face of the pontic clip 713 will now be fully visible.

2.14 In the patient's mouth, the preliminary dental prosthesis is positioned in the occlusal groves in the anterior tooth and posterior tooth adjacent to the edentulous space in the patient's mouth and the mesial and distal ends of the respective buccal groove 717 and lingual groove 718 are now used as guides to mark the exact position for the indentations on the respective buccal and lingual sides of the mesial-proximal surface of the anterior tooth FT' and the distal proximal surface on the posterior tooth ST' in the patient's mouth, and the Dentist with a suitable burr can now complete drilling of the indentations or dimples in these proximal surfaces to form indentations approximately 1.3 mm in width and 1.2 mm in depth. These indentations will fall approximately 1.00 mm lateral to or slightly below and lateral to the occlusal groove preparation in the associated anterior or posterior tooth adjacent the edentulous space in the patient's mouth.

2.15 The occlusal grooves in the occlusal surfaces, the indentations in the proximal surfaces, and the anterior and posterior teeth adjacent the edentulous space in the patient's mouth are now properly etched, washed and dried, and this entire area in the patient's mouth isolated from saliva. Then the prepared tooth surfaces are lightly moistened with water spray, primed with appropriate primers and resins and thus made ready for the dual cure bonding or any other appropriate cements that set chemically so the occlusal grooves, indentations and proximal of the adjacent tooth or teeth can now have the dental prosthesis cemented into assembled position.

2.16 Next, in order to prepare the respective anterior and posterior teeth in the patient's mouth to receive the dental prosthesis, composite material is placed so that it fills the bottom half of the respective occlusal preparations in these teeth. A dual cure composite or a dual cure combined with a glass monomer or any other state-of-the-art art cement or bonding material is used so that the composite under the beam not reached by light curing will be fully set by chemical cure.

2.17 Now the pre-formed dental prosthesis is placed into these partially filled occlusal preparations and pushed down onto the floor of the preparation being careful to avoid any excess materials from getting onto the linguo-proximal indentations and bucco-proximal indentations so there will be no problem in setting the respective lingual and buccal buttresses into assembled position.

2.18 After the preformed dental prosthesis is placed in the cementing composite or similar cementing/bonding material in the occlusal groove preparations in the anterior and posterior teeth adjacent the edentulous space in the patient's mouth and cured in position, the lingual groove in the dental prosthesis is painted with primer and bonding resin which is also cured and the lingual buttress 719 tested by slipping it in and out of assembled position. If it slides properly into assembled position, the lingual buttress 719 will insert fully into the lingual groove 717 and the respective mesial and distal ends of the lingual buttress will rest in the linguo-proximal indentations in the anterior and posterior teeth adjacent to the edentulous space in the patient's mouth.

2.19 The lingual buttress is now removed, a small amount of primer and resin is placed in the associated indentations for the respective ends of the lingual buttress on the adjacent linguo-proximal surfaces of the anterior and posterior teeth, the bonding resin cured and the lingual buttress primed and coated with dual cure bonding cement or similar cementing material. The lingual buttress 719 is now positioned into assembled position so that the connecting rods 725 and 726 extend through the enlarged center section 714 from the lingual side to the exterior of the buccal groove 718 for at least several mm, and the lingual buttress snugly engages the lingual groove 717 and the adjacent face of the leg of the pontic clip 713. Embrasures are then cleared of composite so as not to block interdental hygiene, and the entire assembly on the lingual side of the dental prosthesis is either UV light or chemically cured.

2.20 The same steps above outlined for the lingual buttress are now followed for the buccal buttress, and the entire buccal side of the dental prosthesis is then UV light or chemically cured to lock everything into assembled position. The extending ends of the connecting rods 726 and 727 can now be trimmed flush with the exterior buccal face of the buccal buttress.

2.21 Any residual openings still left on the lingual or buccal side of the preformed pontic are now filled in with composite and enough composite added to bring the lingual and buccal surfaces of the preformed pontic to their normal convexity. This is cured, carved and polished, as needed.

2.22 To complete the dental prosthesis, the visible occlusal surfaces of the anterior and posterior connecting ends 715 and 716 are first coated with an opaque resin. Then over these connecting ends 715 and 716, the respective occlusal surfaces of the adjacent teeth and the pontic unit, a final coat of composite material, reinforced if desired, is added, and this last strip of composite material is covered with a thin sheet of flexible clear plastic about 0.001" thick, such as polyethylene or "SARAN" wrap, and the patient is requested to close fully and then open quickly. The uncured composite material now has an exact imprint of the cusps of the opposing teeth and is cured with ultraviolet light until it is fully hardened.

2.23 A conventional bite test with thin bite paper can then be used so that excess composite material can be removed and the patient's bite adjusted. And finally when the bite is adjusted, the dental prosthesis can again be polished in the patient's mouth.

2.24 If desired, it is possible to custom stain and glaze for a desired color effect or to match the color of existing teeth in the patient's mouth. For this purpose there are various preparations readily available on the open market which can be used in accordance with the instructions for such preparations.

Where one pontic has been referred to, those skilled in the art will readily recognize that a dental prosthesis with more than one pontic can be formed or fabricated by increasing the dimensions of the main support bar or beam for any of the illustrated embodiments of the multi-section infrastructure for forming a dental prosthesis in accordance with the present invention without departing from the scope and spirit of the present invention.

Additionally, while the wide main support bar or beam in some of the embodiments has been illustrated as having a modified curve or arch which drops below the horizontal plane of the connecting ends for the respective main support bars or beams, those skilled in the art will readily recognize that this occurs because the edentulous spaces illustrated are in the lower posterior teeth of the patient's mouth. Conversely, if the edentulous space were illustrated in the upper teeth of the patient's mouth, then the wide occlusal surface of the center section would be above the horizontal plane for the connecting ends for the main support bars or beams of any illustrated one of the embodiments. Other main support bars or beams, especially for bicuspid teeth tend to have a flat occlusal surface on the main support section which also may lie below the plane of the connecting ends for the main support bar. Last, the main support bars in the illustrated embodiments are illustrated with occlusal surfaces having hollowed concave or indented depressions. These as above described serve to increase the thickness of the composite material on the occlusal face of the dental prosthesis formed for the purposes and objects as described.

Having described specific preferred embodiments of the invention with reference to the accompanying drawings, it will be appreciated that the present invention is not limited to those specific embodiments, and that various changes and modifications can be effected therein by one of ordinary skill in the art without departing from the spirit or scope of the invention as defined by the appended claims.

What is claimed is:

1. Multi-section infrastructure for a dental prosthesis for forming at least one pontic to fill an edentulous space in the teeth in a patient's mouth comprising:
    a. main support means for supporting the dental prosthesis having, an enlarged center section, and relatively narrow connecting means connected to at least one end of said enlarged center section to enable the main support means to be connected in assembled position to the patient's teeth relative the edentulous space,
    b. said enlarged center section having, an occlusal surface,
    c. means defining a depression in the occlusal surface of the enlarged center section to permit build-up of composite on said occlusal surface during the formation of the at least one pontic on the dental prosthesis, and
    d. said enlarged center section is wider at the medial section and narrower at the respective opposite ends to accommodate for variations on the proximals of the patient's teeth disposed relative the edentulous space.

2. In the multi-section infrastructure for a dental prosthesis as in claim 1 wherein the enlarged center section is uneven mesial-distally, being wider at one end than at the opposite end.

3. In the multi-section infrastructure for a dental prosthesis in claim 1 wherein the enlarged center section is trapezoidal in mesial-distal plan view being narrower at the anterior end than at the posterior end of the enlarged center section.

4. Multi-section infrastructure for a dental prosthesis for forming at least one pontic to fill an edentulous space in the teeth of a patient's mouth comprising:
    a. main support means for supporting the dental prosthesis to be connected in assembled position to at least one of the patient's teeth relative the edentulous space having occlusal surface means, and
    b. generally U-shaped means adjustably connectable to the main support means for adjusting the position of the occlusal surface of the main support means relative the gingival surface of the edentulous space.

5. A dental prosthesis for replacing at least one tooth in an edentulous space in the teeth in a patient's mouth comprising:
    a. main support means for supporting the dental prosthesis having, a relatively wide center section, and at least one connecting end,
    b. U-shaped means adjustably mounted on said wide center section of main support means for adjusting the positions of said main support means in assembled positions in the edentulous space, and
    c. means for fixedly connecting the U-shaped means to said wide center section in the adjusted position.

6. In the dental prosthesis in claim 5 wherein the means for fixedly connecting the U-shaped means in adjusted position is a cement means from the group of cyano-acrylates.

7. In the dental prosthesis in claim 5 wherein the means for fixably connecting the U-shaped means in adjusted position is a dual cure partly filled chemically set composite.

8. In the dental prosthesis in claim 5 wherein the means for fixedly connecting the U-shaped means in adjusted position is a chemically set bonding adhesive.

9. A dental prosthesis for replacing at least one tooth in an edentulous space in a patient's mouth comprising:
    a. main support means for supporting the dental prosthesis having, a wide center section, and relatively narrow connecting end means connected at one end to said wide center section,
    b. said wide center section having an arcuate shape to form generally a depression section in the wide center section,
    c. generally U-shaped means adjustably mounted on said wide center section of the main support means for adjusting the position of said main support means in assembled position in the edentulous space,
    d. means for fixedly connecting the U-shaped means to said wide center section in the adjusted position, and
    e. means forming at least one pontic about said wide center section and the U-shaped means, disposed in assembled position in said edentulous space.

10. In the dental prosthesis in claim 9 wherein:
    a. the wide center section has generally spaced flat sides on the buccal and lingual faces thereof,
    b. the U-shaped means is disposed on the wide center section in engagement with said flat buccal and lingual sides, and
    c. the means for fixedly connecting the U-shaped pontic clip means to the flat buccal and lingual side edges is a suitable cement means.

11. In the dental prosthesis in claim 10 wherein the cement means is from the group of cyano-acrylates, dual cure partly filled chemically set composite and chemically set bonding adhesives.

12. A dental prosthesis for replacing at least one tooth in an edentulous space in a patient's mouth comprising:
    a. main support means for supporting the dental prosthesis having, a wide center section with an occlusal surface and relatively narrow connecting end means connected to at least one end of said wide center section,
    b. said wide center section having an indented section to provide a generally shaped depression for increasing the thickness of composite disposed thereon during the formation of the replacement tooth,
    c. secondary support means to limit the adverse effect of torque forces on the replacement tooth connected to the wide center section,
    d. generally U-shaped means adjustably mounted on said wide center section of the main support means for adjusting the position of the occlusal surface on said main support means in assembled position in the edentulous space,
    e. means for fixedly connecting the U-shaped means to said wide center section in the adjusted position, and
    f. means forming at least one replacement tooth about said wide center section and the U-shaped means of the dental prosthesis.

13. In the dental prosthesis in claim 9 or 12 wherein the wide center section is uneven in plan view.

14. In the dental prosthesis in claim 9 or 12 wherein the wide center section has a trapezoidal shape in plan view and is sized to fit the edentulous space.

15. In the dental prosthesis in claim 12 wherein the U-shaped means positions the occlusal surface of the main support means and is operatively associated with the secondary support means.

16. In the method of fabricating a dental prosthesis on a cast model of an edentulous space and at least one of the adjacent teeth prepared with occlusal mounting grooves from the given patient's mouth, the steps of:

a. assembling a main support means having a relatively wide center section and at least one relatively narrow connecting end for supporting the dental prosthesis in said edentulous space with a U-shaped means having a base means so that the U-shaped means is in sliding engagement with the wide center section of the main support means for adjusting the position of said main support means in assembled position in the edentulous space, b. fitting the assembled main support means and U-shaped means into position on said cast model so that the at least one connecting end on the wide center section sits in the occlusal mounting grooves in at least one of the adjacent teeth and the U-shaped means and extends into the equivalent edentulous space on the stone cast model, c. adjusting the U-shaped means in the cast model until the base means thereon touches the surface of the equivalent edentulous space in the stone cast model, d. fixedly connecting the U-shaped means in assembled position on the main support means, and e. forming at least one pontic about the wide arcuate center section of the main support means and the coacting U-shaped means.

17. In the method for forming a dental prosthesis with at least one pontic for replacing at least one missing tooth in an edentulous space in a given patient's mouth, the steps of:

a. preparing the teeth in the given patient's mouth adjacent to the edentulous space by cutting sized and shaped grooves in the occlusal surface thereof, b. making a cast model to duplicate the edentulous space and adjacent teeth for use exterior of the patient's mouth, c. assembling in the cast model a multi-section infrastructure having, a main support bar of the desired average length with connecting end means, a buccal groove, a lingual groove and a transverse bore extending end to end therethrough, and centering the main support bar in the edentulous space by adjusting at least one of the connecting end means to fit the sized and shaped grooves in the occlusal surface of the at least one of the teeth adjacent to the edentulous space, d. inserting removable shims in the main support bar to block out the buccal and lingual grooves, e. preliminarily fitting, fabricating, trimming, and finishing in the said cast model a dental prosthesis with at least one pontic replacement thereon, f. removing the dental prosthesis from the cast model and fitting buccal and lingual buttresses into assembled position trimming and finishing the dental prosthesis "in situ" in the teeth adjacent to and in the edentulous space in the patient's mouth so that the at least one pontic fits in and replaces the missing at least one tooth in the edentulous space, g. layering and bonding finishing materials on the formed pontic, and h. adjusting the dental prosthesis "in situ" for bite and cementing the dental prosthesis in assembled position in the occlusal grooves in the prepared teeth in the patient's mouth.

18. A U-shaped member made from a malleable material for use in multi-section infrastructures for forming a dental prosthesis to fill an edentulous space in a patient's mouth comprising:

a. base means, and b. spaced leg means connected to opposite sides of said base means for operative association with the gum line in the edentulous space and for adjusting the multi-section infrastructures in assembled position in the edentulous space.

19. A U-shaped means as claimed in claim 18 wherein the base means is made from a material that can be polished.

20. A U-shaped means as claimed in claim 18 wherein the base means is sized and shaped for use as a function of the average shape of the gum line for the edentulous space.

21. A U-shaped means as claimed in claim 18 wherein the base means can be altered to fit asymmetrically shaped gingiva for a given edentulous space.

22. A U-shaped means as claimed in claim 18 wherein the spaced leg means includes:

a. first leg means connected to one side of the base means, b. second leg means connected to the other side of the base means, and c. said first leg means and second leg means scored to aid in assembling the U-shaped means to the other elements of the multi-section infrastructure.

23. In combination with the multi-section infrastructure for forming the dental prosthesis, said multi-section infrastructure including, a. main support means for the dental prosthesis having a center section, b. a first groove means on the lingual side of the center section, and a second groove means on the buccal side of the center section, of a fixture comprising:

i. a first removable shim member for operative connection into the first groove, ii. a second removable shim member for operative connection into the second groove, and iii. means for aligning the first removable shim member and second removable shim member in assembled position to permit the dental prosthesis to be formed about the multi-section infrastructure.

24. The combination with the multi-section infrastructure for forming a dental prosthesis in claim 23 including, means to enable the first removable shim member and second removable shim member to be removed from assembled position after the pontic has been preliminarily formed on the dental prosthesis.

* * * * *